United States Patent
Duncan et al.

(10) Patent No.: US 12,037,414 B2
(45) Date of Patent: Jul. 16, 2024

(54) PROCESSES FOR PREPARING PHARMACEUTICALLY RELEVANT PEPTIDES

(71) Applicant: STEALTH BIOTHERAPEUTICS INC., Needham, MA (US)

(72) Inventors: Scott Duncan, Bedford, MA (US); D. Travis Wilson, Newton, MA (US)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 275 days.

(21) Appl. No.: 16/813,380

(22) Filed: Mar. 9, 2020

(65) Prior Publication Data

US 2020/0308221 A1    Oct. 1, 2020

Related U.S. Application Data

(62) Division of application No. 15/555,494, filed as application No. PCT/US2016/021245 on Mar. 7, 2016, now Pat. No. 10,633,415.

(60) Provisional application No. 62/129,575, filed on Mar. 6, 2015.

(51) Int. Cl.
| | | |
|---|---|---|
| *C07K 1/04* | (2006.01) | |
| *C07K 1/02* | (2006.01) | |
| *C07K 5/11* | (2006.01) | |

(52) U.S. Cl.
CPC .............. *C07K 5/1019* (2013.01); *C07K 1/02* (2013.01); *C07K 1/04* (2013.01)

(58) Field of Classification Search
CPC ........... C07K 5/1019; C07K 1/02; C07K 1/04
See application file for complete search history.

(56) References Cited

U.S. PATENT DOCUMENTS

| | | | |
|---|---|---|---|
| 4,242,507 A * | 12/1980 | Itoh ..................... | C07D 249/18 530/341 |
| 5,436,221 A | 7/1995 | Kitaguchi et al. | |
| 6,248,716 B1 | 6/2001 | Deigin et al. | |
| 7,262,169 B1 | 8/2007 | Ashwood et al. | |
| 8,871,904 B2 | 10/2014 | Tanoury et al. | |
| 9,982,014 B2 | 5/2018 | Hirai et al. | |
| 2003/0069231 A1 | 4/2003 | Rudolf et al. | |
| 2004/0176305 A1 | 9/2004 | Schiller et al. | |
| 2007/0225261 A1 | 9/2007 | Miller et al. | |
| 2007/0275903 A1 | 11/2007 | Bebbington et al. | |
| 2009/0215986 A1 | 8/2009 | Epstein et al. | |
| 2012/0329730 A1 | 12/2012 | Szeto et al. | |
| 2013/0059784 A1 | 3/2013 | Wilson | |
| 2013/0190244 A1 | 7/2013 | Borow et al. | |
| 2013/0303436 A1 | 11/2013 | Wilson | |
| 2014/0294796 A1 | 10/2014 | Wilson et al. | |
| 2015/0183831 A1 | 7/2015 | Kirihata et al. | |

FOREIGN PATENT DOCUMENTS

| | | | |
|---|---|---|---|
| EP | 0 779 076 A1 | 6/1997 | |
| GB | 1 037 168 A | 7/1966 | |
| JP | H05-503535 A | 9/1991 | |
| JP | H05-186499 A | 7/1993 | |
| JP | H09-176187 A | 7/1997 | |
| JP | 2001-503011 A | 3/2001 | |
| JP | 2003-516319 A | 5/2003 | |
| WO | WO 91/13088 | 9/1991 | |
| WO | WO96/02267 | 1/1996 | |
| WO | WO-2007027742 A2 * | 3/2007 | ......... C07K 5/06191 |
| WO | WO-2011/091357 A1 | 7/2011 | |
| WO | WO2012/174117 A2 | 12/2012 | |
| WO | WO-2013086020 A1 * | 6/2013 | .............. A61P 43/00 |
| WO | WO-2013/118823 | 8/2013 | |
| WO | WO2013/126597 A1 | 8/2013 | |
| WO | WO-2014/165607 A2 | 10/2014 | |
| WO | WO-2015/100376 A1 | 7/2015 | |
| WO | WO 2015/100376 A1 | 7/2015 | |
| WO | WO2015/134096 | 9/2015 | |

OTHER PUBLICATIONS

Suzuki et al (Chemical & Pharmaceutical Bulletin, 1988, 36(12) 4834-40) (Year: 1988).*
Itoh et al (abstract from STN search report, U.S. Pat. No. 4,242,507, 1980). (Year: 1980).*
Yoshimi, Creation of high-functional peptides by photoreaction, University of Fukui, 2011 Fund for Research and Supporting Scholars, 2011, pp. 32-33 (no English translation available).
Extended European Search Report issued on EP Application 14874049. 1, mailed Aug. 25, 2017.
Gowda, D., "Removal of some commonly protecting groups in peptide syntheses by catalytic transfer hydrogenation with formic acid and 10% palladium on carbon," Indian Journal of Chemistry, vol. 41B, pp. 1064-1067 (May 2002).
Harrison et al., "2,6-Dimethyltyrosine analogues of a stereodiversified ligand library: highly potent, selective, non-peptidic u opioid receptor agonists," J. Med. Chem., pp. 677-680 (2003).
International Search Report and Written Opinion, PCT/US2014/ 072264 (Mar. 25, 2015), 10 pages.
Soloshonok et al., "Large-scale asymmetric synthesis of novel sterically constrained 2',6'-dimethyl- and a,2',6'-trimethyltyrosine and -phenylalanine derivatives via alkylation of chiral equivalents and nucleophilic glycine and alanine," Tetrahedron, pp. 6375-6382 (2001).
Tsuda et al., "Amino acid coupling chemistry, solution-phase peptide synthesis," Peptide and Proteins in Organic Chemistry, pp. 203-252 (Jan. 31, 2011).
Still, et al., "Rapid chromatographic Technique for Preparative Separations with Moderate Resolution," *J. Org. Chem.*, vol. 43, No. 14, pp. 2923-2925 (1978).
Foreign Action other than Search Report on CN 201480075290.4, dated Jul. 17, 2019.
Sharon D. Bryant et al., "Dmt and opioid peptides: A potent alliance Biopolymers," vol. 71, No. 2, pp. 86-102, (Jan. 12, 2004).

(Continued)

*Primary Examiner* — Sudhakar Katakam
(74) *Attorney, Agent, or Firm* — Foley & Lardner LLP

(57) ABSTRACT

The present technology provides methods of generating the peptides, and pharmaceutically acceptable salts of the peptides and intermediates thereof. In some embodiments, the peptide is D-Arg-2'6'-Dmt-Lys-Phe-NH$_2$.

1 Claim, No Drawings

(56) References Cited

OTHER PUBLICATIONS

Van Orden et al., "The Synthesis of Arginyl Dipeptides; The Action of Papain and Trypsin," *J. Biol. Chem.*, vol. 208, pp. 751-764 (1954).
Request to Record Change Under Rule 92 BIS and Certificate of Incorporation, International Patent Application No. PCT/US2014/072264, filed Jun. 22, 2016 (3 pages).
Gregory et al., "Org. 715 Polypeptides: Part VIII.I Variations of the Aspartyl Position in the C-Terminal Tetrapeptide Amide Sequence of the Gastrins," Inform. Bull. Chem. Soc., 11 pages(Jan. 1, 1963).
International Preliminary Report on Patentability in International Application No. PCT/US2016/021245 dated Sep. 12, 2017 (8 pages).
International Search Report and Written Opinion in International Application No. PCT/US2016/021245 mailed May 23, 2016 (9 pages).
Isidro-Llobet, et al., "Amino Acid-Protecting Groups," *Chem. Rev.*, vol. 109, pp. 2455-2504 (2009).
Van Orden, et al., "The Synthesis of Arginyl Dipeptides; the Action of Papain and Tryppsin," *Journ. of Biol. Chem.*, vol. 208, pp. 751-764 (1954).
Montalbetti, et al., "Amide Bond Formation and Peptide Coupling," *Tetrahedron* 61, Report No. 740i, pp. 10827-10852 (2005).
Franklin, et al., "A Potent New Dipeptide Inhibitor of Cell Sickling and Haemoglobin S Gelation," *Eur. J. Biochem.*, vol. 136, pp. 209-214 (1983).
Haug, et al., "Synthesis of a Gln-Phe hydroxy-ethylene dipeptide isostere," Org. Lett., 2004, vol. 6(25), pp. 4783-4786 and supplemental information.
Official Action in JP Patent Application No. 2017-546662 dated Apr. 20, 2020 (with English translation) (9 pages).
Ota, et al., "Synthesis of Morphiceptin (Tyr-Pro-Phe-Pro-NH2) by Dipeptidyl Aminopeptidase IV Derived from Aspergillus oryzae," Journal of Agricultural and Food Chemistry, 2005, vol. 53(15), pp. 6112-6116.
Suppo, et al., "Inverse peptide synthesis via activated a-aminoesters, Angew." Chem. Int. Ed., 2014, vol. 53(21), pp. 5389-5393.
Franklin, Ian M., et al., A potent new dipeptide inhibitor of cell sickling and haemoglobin S gelation, Eur. J. Biochem, 136, pp. 209-214, 1983.
Isidro-Llobet, Albert, et al., Amino Acid-Protecting Groups, Chem. Rev., 2009, 109, 2455-2504.
Montalbetti, Christian A.G.N., et al., Amide bond formation and peptide coupling, Tetrahedron 61, 2005, pp. 10827-10852.
Van Orden, et al., The synthesis of arginyl dipeptides; the action of papain and trypsin, Journal of Biological Chemistry, 1954, 208, pp. 751-764.
Foreign Action in CA 2978905 dated Feb. 15, 2022.
Foreign Action in JP 2021-042262 dated Mar. 28, 2022.
Foreign Action in JP 2021-042262, dated Sep. 14, 2023.
Office Action on JP 2021-042262 dated Dec. 26, 2022.
Communication pursuant to Article 94(3) EPC on EP Patent Application No. 20196964.9 dated Dec. 20, 2023 (4 pages).
Foreign Action in CN 202111147950.3, Dated Jan. 10, 2024.

* cited by examiner

PROCESSES FOR PREPARING PHARMACEUTICALLY RELEVANT PEPTIDES

CROSS-REFERENCE TO RELATED APPLICATIONS

This application is a divisional of U.S. patent application Ser. No. 15/555,494, filed Sep. 1, 2017, which is the U.S. National Stage of International Patent Application No. PCT/US2016/021245, filed Mar. 7, 2016, which claims priority to U.S. Provisional Patent Application No. 62/129,575, filed Mar. 6, 2015, where the contents of these applications are incorporated herein by reference in their entirety.

FIELD OF TECHNOLOGY

The present technology relates general methods of generating pharmaceutically relevant peptides and intermediates thereof.

SUMMARY

In an aspect, a process is provided for the preparation of a compound of formula VIII or a salt thereof:

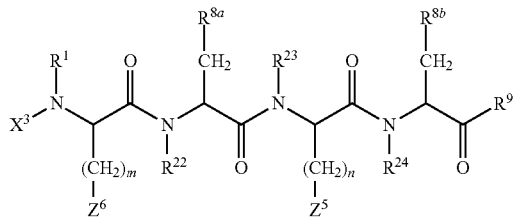

(VIII)

the method comprising reacting a compound of formula I-A or a salt thereof,

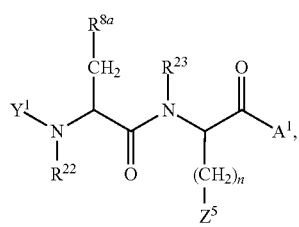

(I-A)

with a compound of formula I-B or a salt thereof,

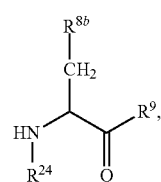

(I-B)

to form a compound of formula I-C or a salt thereof:

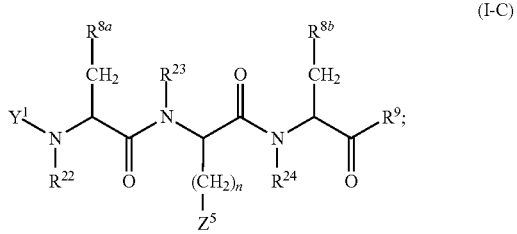

(I-C)

converting the compound of formula I-C to a compound of formula I-D or a salt thereof:

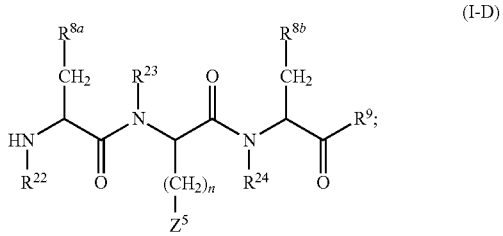

(I-D)

reacting the compound of formula I-D or a salt thereof with a compound of formula I-E or a salt thereof to form the compound of formula VIII or a salt thereof:

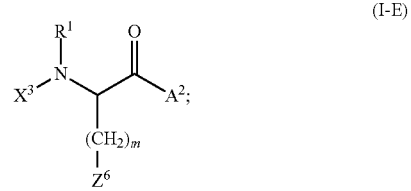

(I-E)

wherein
$A^1$ and $A^2$ each independently, together with the carbonyl group to which each is attached, forms a carboxylic acid, active ester, anhydride, or acid halide, for example, $A^1$ and $A^2$ are each independently —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^1$ and $R^2$ are each independently
  (i) hydrogen;
  (ii) substituted or unsubstituted $C_1$-$C_6$ alkyl;
  (iii) substituted or unsubstituted aralkyl;
  (iv) substituted or unsubstituted $C_3$-$C_8$ cycloalkyl or cycloalkylalkyl;
  (v) substituted or unsubstituted $C_2$-$C_6$ alkenyl;
  (vi) an amino protecting group;
  or $R^1$ and $R^2$ together form a 3, 4, 5, 6, 7, or 8 membered substituted or unsubstituted heterocyclyl or heteroaryl group;

$R^{8a}$ and $R^{8b}$ are each independently selected from

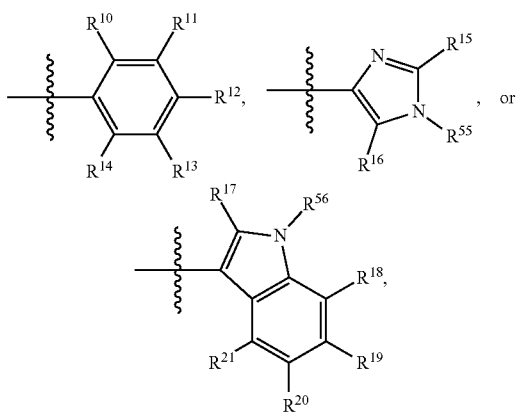

where $R^{10}, R^{11}, R^{13}, R^{14}, R^{15}, R^{16}, R^{17}, R^{18}, R^{19}, R^{20}$, and $R^{21}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R''; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R'' is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{12}$ is selected from hydrogen, —OH, halogen (e.g., F, Cl, Br, I), $C_1$-$C_6$ alkyl, —O—$C_1$-$C_6$ alkyl, —NH—$C_1$-$C_6$ alkyl, —N($C_1$-$C_6$ alkyl)$_2$, $C_1$-$C_4$-perhaloalkyl, aralkyl, —O-aralkyl, —NH-aralkyl, —N(aralkyl)$_2$, —N($C_1$-$C_6$ alkyl)(aralkyl), —C(O)-alkyl, —C(O)-aryl, or —C(O)-aralkyl, wherein each alkyl, aryl or aralkyl group is substituted or unsubstituted;

$R^{22}$, $R^{23}$, and $R^{24}$ are each independently hydrogen or a $C_1$-$C_4$ alkyl;

n is 1, 2, 3, 4, or 5;

m is 1, 2, 3, 4, or 5;

$X^1$, $X^2$ and $X^4$ are independently at each occurrence hydrogen or an amino protecting group, such as an amino protecting group susceptible to acid-mediated removal or an amino protecting group resistant to acid-mediated removal and susceptible to base-mediated or hydrogen-mediated removal;

$X^3$ is $R^2$, hydrogen or an amino protecting group;

$Y^1$ is an amino protecting group, such as an amino protecting group susceptible to acid-mediated removal or an amino protecting group resistant to acid-mediated removal and susceptible to base-mediated or hydrogen-mediated removal; and $Z^5$ and $Z^6$ are each independently —NHX$^1$, —C(N—X$^4$)—NH—X$^2$, —NX$^1$C(N—X$^4$)—NH—X$^2$, —NX$^1$($C_1$-$C_6$ alkyl), —NX$^1$($C_6$-$C_{10}$ aryl), —NX$^1$($C_7$-$C_{12}$ aralkyl), or nitrogen-containing heterocyclyl or heteroaryl group wherein each alkyl, aryl, aralkyl, heterocyclyl, or heteroaryl group is substituted or unsubstituted.

In an aspect, a process is provided for the preparation of a compound of formula VIII or a salt thereof:

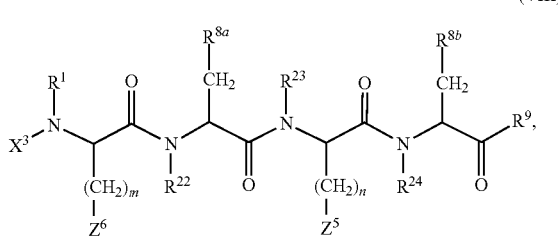

(VIII)

the method comprising reacting a compound of formula II-D or a salt thereof with a compound of formula I-B or a salt thereof to form the compound of formula VIII or a salt thereof:

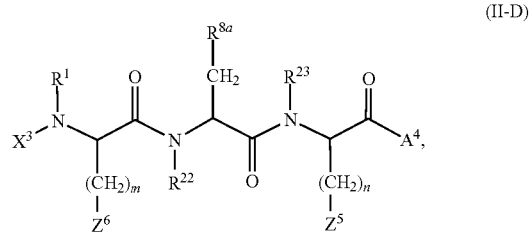

(II-D)

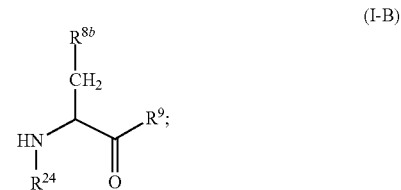

(I-B)

wherein $A^4$ together with the carbonyl group to which it is attached forms a carboxylic acid, active ester, anhydride, or acid halide, for example, $A^4$ may be —OH, —O—$R^{58}$, —OC(O)—$R^{59}$, F, Cl, or Br, $R^{58}$ is a substituted or unsubstituted aryl, heteroaryl, or heterocyclyl group, and, $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^1$ and $R^2$ are each independently
  (i) hydrogen;
  (ii) substituted or unsubstituted $C_1$-$C_6$ alkyl;
  (iii) substituted or unsubstituted aralkyl;
  (iv) substituted or unsubstituted $C_3$-$C_8$ cycloalkyl or cycloalkylalkyl;
  (v) substituted or unsubstituted $C_2$-$C_6$ alkenyl;
  (vi) an amino protecting group;
  or $R^1$ and $R^2$ together form a 3, 4, 5, 6, 7, or 8 membered substituted or unsubstituted heterocyclyl or heteroaryl group;

$R^{8a}$ and $R^{8b}$ are each independently selected from

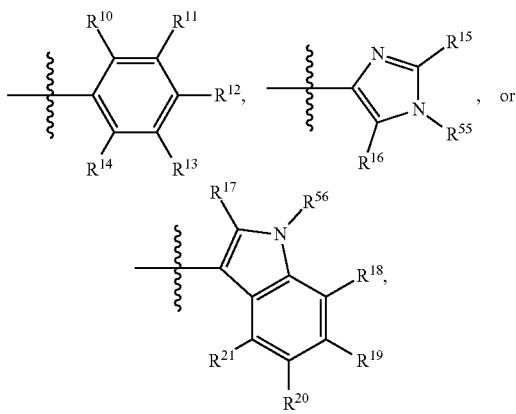

, or where $R^{10}$, $R^{11}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R"; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R" is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{12}$ is selected from hydrogen, —OH, halogen (e.g., F, Cl, Br, I), $C_1$-$C_6$ alkyl, —O—$C_1$-$C_6$ alkyl, —NH—$C_1$-$C_6$ alkyl, —N($C_1$-$C_6$ alkyl)$_2$, $C_1$-$C_4$-perhaloalkyl, aralkyl, —O-aralkyl, —NH-aralkyl, —N(aralkyl)$_2$, —N($C_1$-$C_6$ alkyl)(aralkyl), —C(O)-alkyl, —C(O)-aryl, or —C(O)-aralkyl, wherein each alkyl, aryl or aralkyl group is substituted or unsubstituted;

$R^{22}$, $R^{23}$, and $R^{24}$ are each independently hydrogen or a $C_1$-$C_4$ alkyl;

n is 1, 2, 3, 4, or 5;

m is 1, 2, 3, 4, or 5;

$X^1$, $X^2$ and $X^4$ are independently at each occurrence hydrogen or an amino protecting group, such as an amino protecting group susceptible to acid-mediated removal or an amino protecting group resistant to acid-mediated removal and susceptible to base-mediated or hydrogen-mediated removal;

$X^3$ is $R^2$, hydrogen or an amino protecting group; and $Z^5$ and $Z^6$ are each independently —NHX$^1$, —C(N—X$^4$)—NH—X$^2$, —NX$^1$C(N—X$^4$)—NH—X$^2$, —NX$^1$($C_1$-$C_6$ alkyl), —NX$^1$($C_6$-$C_{10}$ aryl), —NX$^1$($C_7$-$C_{12}$ aralkyl), or nitrogen-containing heterocyclyl or heteroaryl group wherein each alkyl, aryl, aralkyl, heterocyclyl, or heteroaryl group is substituted or unsubstituted.

In some embodiments, the compound of formula II-D or a salt thereof is prepared by a method comprising converting the compound of formula II-C or a salt thereof to a compound of formula II-D or a salt thereof

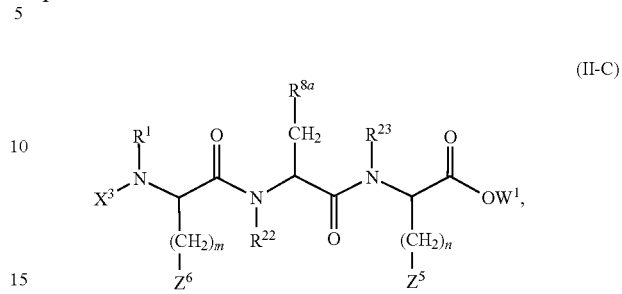

(II-C)

wherein $W^1$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group, and the other variables are as defined in formula II-D.

In some embodiments, the compound of formula II-C or a salt thereof is prepared by a method comprising reacting a compound of formula II-A or a salt thereof with a compound of formula I-E or a salt thereof to form a compound of formula II-C or a salt thereof:

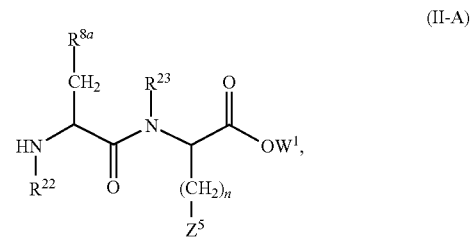

(II-A)

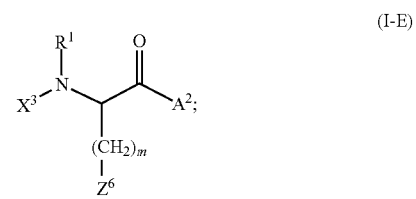

(I-E)

wherein $A^2$ together with the carbonyl group to which it is attached forms a carboxylic acid, active ester, anhydride, or acid halide, for example, $A^2$ may be —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group, and the other variables are as defined in formula II-D.

In some aspects, the compound of formula I-A or II-A or a salt thereof is prepared by coverting a compound of I-F or a salt thereof to the compound of I-A or II-A or a salt thereof:

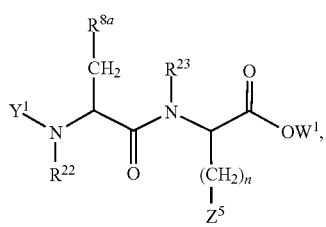

(I-F)

wherein n, $W^1$, $Y^1$, $Z^5$, $R^{22}$, and $R^{8a}$ are as defined herein.

In some aspects, the compound of formula of I-F or a salt thereof is prepared by a method comprising reacting a compound of formula I-G or a salt thereof with a compound of formula I-H or a salt thereof:

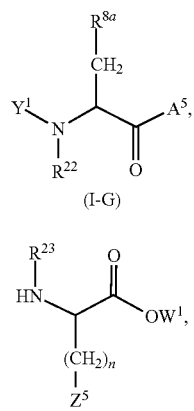

(I-G)

(I-H)

wherein $R^{8a}$, $R^{22}$, $R^{23}$, $W^1$, $Y^1$, $Z^5$ and n are as defined herein, and $A^5$ together with the carbonyl group to which it is attached forms a carboxylic acid, active ester, anhydride, or acid halide, for example, $A^5$ may be —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In another aspect, a process is provided for the preparation of a compound of formula VIII or a salt thereof:

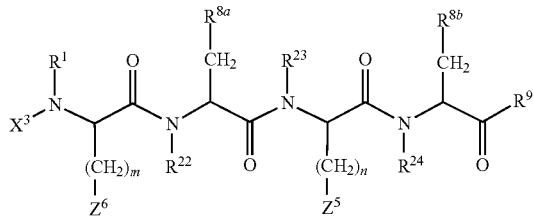

(VIII)

the method comprising reacting a compound of formula III-A or a salt thereof with a compound of formula III-B or a salt thereof to form a compound of formula VIII or a salt thereof:

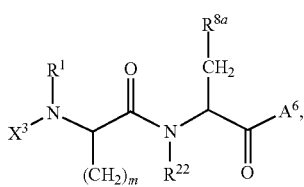

(III-A)

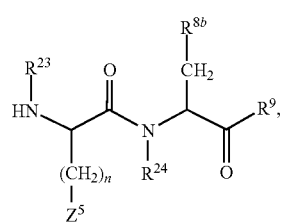

(III-B)

wherein
$A^6$ together with the carbonyl group to which it is attached forms a carboxylic acid, active ester, anhydride, or acid halide, for example, $A^6$ may be —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group;
$R^1$ and $R^2$ are each independently
 (i) hydrogen;
 (ii) substituted or unsubstituted $C_1$-$C_6$ alkyl;
 (iii) substituted or unsubstituted aralkyl;
 (iv) substituted or unsubstituted $C_3$-$C_8$ cycloalkyl or cycloalkylalkyl;
 (v) substituted or unsubstituted $C_2$-$C_6$ alkenyl;
 (vi) an amino protecting group;
 or $R^1$ and $R^2$ together form a 3, 4, 5, 6, 7, or 8 membered substituted or unsubstituted heterocyclyl or heteroaryl group;
$R^{8a}$ and $R^{8b}$ are each independently selected from

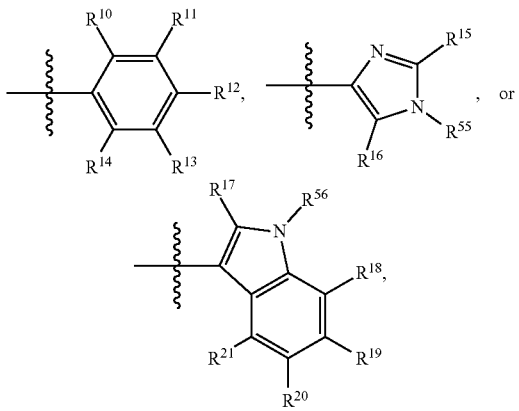

where $R^{10}$, $R^{11}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R''; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R" is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{12}$ is selected from hydrogen, —OH, halogen (e.g., F, Cl, Br, I), $C_1$-$C_6$ alkyl, —O—$C_1$-$C_6$ alkyl, —NH—$C_1$-$C_6$ alkyl, —N($C_1$-$C_6$ alkyl)$_2$, $C_1$-$C_4$-perhaloalkyl, aralkyl, —O-aralkyl, —NH-aralkyl, —N(aralkyl)$_2$, —N($C_1$-$C_6$ alkyl)(aralkyl), —C(O)-alkyl, —C(O)-aryl, or —C(O)-aralkyl, wherein each alkyl, aryl or aralkyl group is substituted or unsubstituted;

$R^{22}$, $R^{23}$, and $R^{24}$ are each independently hydrogen or a $C_1$-$C_4$ alkyl;

n is 1, 2, 3, 4, or 5;

m is 1, 2, 3, 4, or 5;

$X^1$, $X^2$ and $X^4$ are independently at each occurrence hydrogen or an amino protecting group, such as an amino protecting group susceptible to acid-mediated removal or an amino protecting group resistant to acid-mediated removal and susceptible to base-mediated or hydrogen-mediated removal;

$X^3$ is $R^2$, hydrogen or an amino protecting group;

$Z^5$ and $Z^6$ are each independently —NHX$^1$, —C(N—X$^4$)—NH—X$^2$, —NX$^1$C(N—X$^4$)—NH—X$^2$, —NX$^1$($C_1$-$C_6$ alkyl), —NX$^1$($C_6$-$C_{10}$ aryl), —NX$^1$($C_7$-$C_{12}$ aralkyl), or nitrogen-containing heterocyclyl or heteroaryl group wherein each alkyl, aryl, aralkyl, heterocyclyl, or heteroaryl group is substituted or unsubstituted.

In some aspects, the compound of formula III-A or a salt thereof is prepared by a method comprising converting the compound of formula III-C or a salt thereof to a compound of formula III-A or a salt thereof:

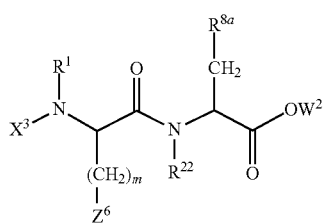

(III-C)

wherein $W^2$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group and $R^1$, $R^{8a}$, $R^{22}$, $W^2$, $X^3$, $Z^6$ and m are as defined herein. In some embodiments, $W_2$ is benzyl (Bn) and $X_3$ is Boc, and converting a compound of formula IIIC comprises reductively cleaving the benzyl to H (e.g., with H$_2$, and a supported transition metal such as Pd or Pt on carbon). In some embodiments, $R^1$ and $R^{22}$ are both H, m is 3, $Z^6$ is —NHC(NH)NH$_2$, and $R^{8a}$ is 2,6-dimethyl-4-hydroxyphenyl. For example, the compound of formula III-C can be Boc-D-Arg-DMT-OBn.

In some aspects, the compound of formula III-C or a salt thereof is prepared by a method comprising reacting a compound of formula III-D or a salt thereof with a compound of formula I-E or a salt thereof to form a compound of formula III-C or a salt thereof:

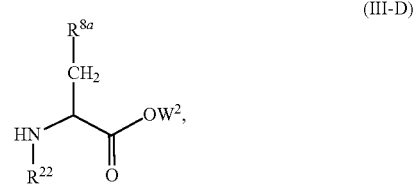

(III-D)

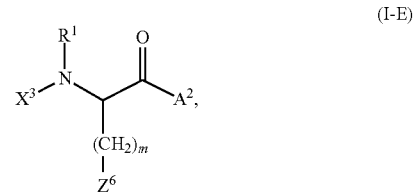

(I-E)

wherein $A^2$, $R^1$, $R^{8a}$, $R^{22}$, $W^2$, $X^3$, $Z^6$ and m are as defined herein.

In some aspects, the compound of formula III-B or a salt thereof is prepared by a method comprising coverting a compound of formula III-E or a salt thereof to the compound of formula III-B or a salt thereof:

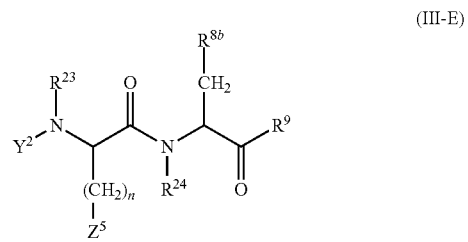

(III-E)

wherein $Y^2$ is an amino protecting group, such as an amino protecting group susceptible to acid-mediated removal or an amino protecting group resistant to acid-mediated removal and susceptible to base-mediated or hydrogen-mediated removal, and $R^{8b}$, $R^9$, $R^{23}$, $R^{24}$, $Z^5$ and n are as defined herein. In some embodiments, $Y^2$ is Cbz and converting the compound of III-E comprises reductively cleaving the Cbz to H (e.g., with H$_2$ and a supported transition metal such as Pd or Pt on carbon). In some embodiments, $R^9$ is —NH$_2$, $R^{23}$ is H, n is 4, $Z^5$ is —NHBoc, and $R^{8b}$ is unsubstituted phenyl. For example, the compound of formula III-E can be Cbz-Lys(Boc)-Phe-NH$_2$.

In some aspects, the compound of formula III-E or a salt thereof is prepared by a method comprising reacting a compound of formula I-B or a salt thereof with a compound of formula III-F or a salt thereof to form a compound of formula III-E or a salt thereof:

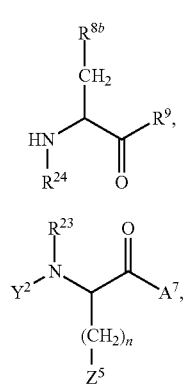

(I-B)

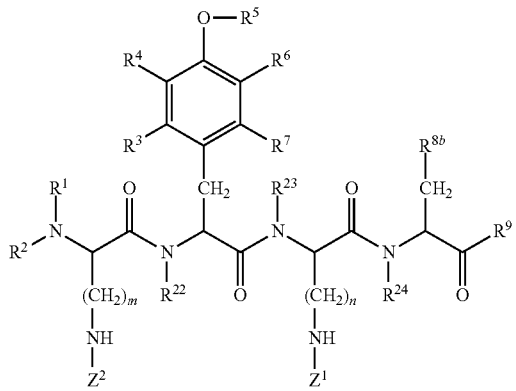

(I)

(III-F)

wherein $R^{8b}$, $R^9$, $R^{23}$, $R^{24}$, $W^1$, $Y^2$, $Z^5$ and n are as defined herein, and $A^7$ together with the carbonyl group to which it is attached forms a carboxylic acid, active ester, anhydride, or acid halide, for example, $A^7$ is —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In any of the above embodiments, it may be that the conditions to form the compound of formula VIII or a salt thereof include a coupling agent. Such coupling agents as used in any of the aspects and embodiments described herein may include carbodiimides, uronium salts, aminium salts, immonium salts, carbonium salts, phosphonium salts, phosphorus reagents, pentafluorophenol based reagents, etc. that are know in the art. In any of the above embodiments, it may be that the conditions to form the compound of formula VIII or a salt thereof further include a solvent as described herein. In any of the above embodiments, it may be that the conditions to form the compound of formula VIII or a salt thereof further include a base. In any of the above embodiments, it may be that the conditions to form the compound of formula VIII or a salt thereof include EDC and HOBT, EDC-HCl and HOBT, BOP and HOBT, or HATU and HOAT. In any of the above embodiments, it may be that the coupling agent is propylphosphonic anhydride ($T_3P$).

In some embodiments, $Y^1$ is an amino protecting group susceptible to acid-mediated removal and it may be that converting the compound of formula I-C or a salt thereof to formula I-D or a salt thereof comprises combining the compound of formula I-C or a salt thereof with a cleaving acid. In some embodiments, $Y^1$ is an amino protecting group susceptible to acid-mediated removal and converting the compound of formula I-F or a salt thereof to formula II-A or a salt thereof comprises combining the compound of formula I-F or a salt thereof with a cleaving acid. Examples of cleaving acids are known in the art and described herein. In any of the above embodiments, it may be that combining with the cleaving acid further includes a protic solvent, a polar aprotic solvent, or a mixture of the two.

In another aspect, when at least one of $X^1$, $X^2$, $X^3$ and $X^4$ in the compound of formula VIII or a salt thereof is an amino protecting group resistant to acid-mediated removal and susceptible to hydrogen-mediated removal, the process further comprises reacting the compound of formula VIII or a salt thereof with a hydrogen source and a transition metal catalyst to form a compound of formula I or a salt thereof:

or a pharmaceutically acceptable salt thereof, wherein
$R^1$ and $R^2$ are each independently
(i) hydrogen;
(ii) substituted or unsubstituted $C_1$-$C_6$ alkyl;
(iii) substituted or unsubstituted aralkyl;
(iv) substituted or unsubstituted $C_3$-$C_8$ cycloalkyl or cycloalkylalkyl;
(v) substituted or unsubstituted $C_2$-$C_6$ alkenyl;
(vi) an amino protecting group;
or $R^1$ and $R^2$ together form a 3, 4, 5, 6, 7, or 8 membered substituted or unsubstituted heterocyclyl or heteroaryl group;
$R^3$, $R^4$, $R^6$, and $R^7$ are each independently hydrogen, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)— aralkyl, carboxylate, ester, amide, nitro, hydroxyl, halogen, or perhaloalkyl group, wherein each alkyl, aryl or aralkyl group is substituted or unsubstituted;
$R^5$ is selected from hydrogen, $C_1$-$C_6$ alkyl, aralkyl, —C(O)-alkyl, —C(O)-aryl, or —C(O)— aralkyl, wherein each alkyl, aryl or aralkyl group is substituted or unsubstituted;
$R^{8b}$ is

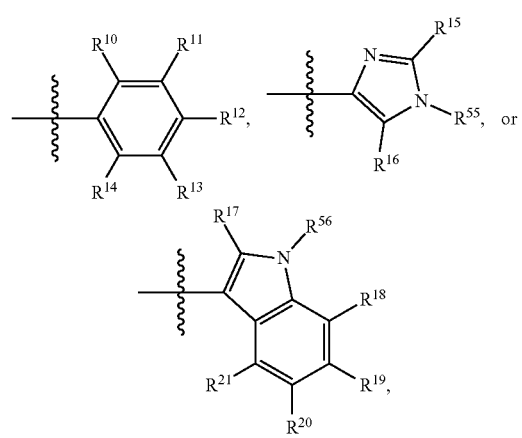

where $R^{10}$, $R^{11}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R"; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R" is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{12}$ is selected from hydrogen, —OH, halogen (e.g., F, Cl, Br, I), $C_1$-$C_6$ alkyl, —O—$C_1$-$C_6$ alkyl, —NH—$C_1$-$C_6$ alkyl, —N($C_1$-$C_6$ alkyl)$_2$, $C_1$-$C_4$-perhaloalkyl, aralkyl, —O-aralkyl, —NH-aralkyl, —N(aralkyl)$_2$, —N($C_1$-$C_6$ alkyl)(aralkyl), —C(O)-alkyl, —C(O)-aryl, or —C(O)-aralkyl, wherein each alkyl, aryl or aralkyl group is substituted or unsubstituted;

$R^{22}$, $R^{23}$, and $R^{24}$ are each independently hydrogen or a $C_1$-$C_4$ alkyl;

n is 1, 2, 3, 4, or 5;

m is 1, 2, 3, 4, or 5;

$Z^1$ and $Z^2$ are each independently hydrogen, —C(NH)—NH$_2$ or a substituted or unsubstituted alkyl, aryl, or aralkyl group.

In another aspect, when at least one of $X^1$, $X^2$, $X^3$ and $X^4$ in the compound of formula VIII or a salt thereof is an amino protecting group susceptible to acid-mediated removal, the process further comprises reacting the compound of formula VIII or a salt thereof with a cleaving acid to form a compound of formula I or a salt thereof. In some embodiments, one or more of $X^1$, $X^2$, $X^3$ and $X^4$ is a Boc group. In some such embodiments, the Boc group is removed with HCl, optionally under anhydrous conditions, to provide the HCl salt of the compound of formula VIII or I.

Alternatively, in any of the aspects herein, the salt of the compound of formula I, VIII, VIII-B or any other such compound may be an aliphatic carboxylate, hydrochloride, hydrobromide, alkylsulfonate, arylsulfonate, fumarate, succinate, tartrate, oxalate, phosphate, or sulfate salt.

DETAILED DESCRIPTION

Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyl; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, butadienyl, pentadienyl, and hexadienyl. Cycloalkenyl groups may be substituted or unsubstituted.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). The phrase "aryl groups" also includes substituted aryl groups. Groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above. In some embodiments, the aryl group is phenyl, which can be substituted or unsubstituted. In some embodiments, substituted phenyl groups have one or two substituents. In some embodiments, substituted phenyl groups have one substituent.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl or heterocycle groups are non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase also includes bridged polycyclic ring systems containing a heteroatom such as, but not limited to, quinuclidyl. The phrase also includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, piperidyl, piperazinyl, morpholinyl, thiomorpholinyl, tetrahydropyranyl, and tetrahydrothiopyranyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above. The heteroatom(s) can also be in oxidized form, if chemically possible.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds and also includes heteroaryl groups that have other groups bonded to one of the ring members, such as alkyl groups, referred to as "substituted heteroaryl groups." Representative substituted heteroaryl groups may be substituted one or more times with various substituents such as those listed above. The heteroatom(s) can also be in oxidized form, if chemically possible.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclylalkyl groups include, but are not limited to, morpholin-4-yl-ethyl, and tetrahydrofuran-2-yl-ethyl. Representative substituted heterocyclylalkyl groups may be substituted one or more times with substituents such as those listed above. The heteroatom(s) can also be in oxidized form, if chemically possible.

Heteroaralkyl groups are alkyl groups as defined above in which a hydrogen or carbon bond of an alkyl group is replaced with a bond to a heteroaryl group as defined above. Heteroaralkyl may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above. The heteroatom(s) can also be in oxidized form, if chemically possible.

Groups described herein having two or more points of attachment (i.e., divalent, trivalent, or polyvalent) within the compound of the invention are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the invention are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Like alkyl groups, alkoxy groups may be linear or branched. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —C(O)OH group or to its ionized form, —C(O)O$^-$.

The term "ester" as used herein refers to —C(O)OR$^{60}$ groups. R$^{60}$ is a substituted or unsubstituted alkyl, cycloalkyl, alkenyl, alkynyl, aryl, aralkyl, heteroaryl, heteoryaralkyl, heterocyclylalkyl or heterocyclyl group as defined herein. The term ester also refers to OC(O)R$^{60}$ groups. For example, an ester may be —OC(O)-alkyl, —OC(O)-aryl, or —OC(O)-aralkyl, wherein each alkyl, aryl, or aralkyl group is substituted or unsubstituted.

The term "active ester" refers to an ester that wherein —OR$^{60}$ is a good leaving group and is susceptible to reaction with an primary or secondary amine to form an amide. Active esters are known in the art. Examples of active esters include compounds wherein R$^{60}$ is —NR$^{67}$COR$^{67}$, wherein R$^{67}$ and COR$^{67}$ together with the nitrogen to which they are attached form a 5 or 6 membered heterocycle optionally substituted with one more oxo and optionally fused with a substituted or unsubstituted cycloalkyl, cycloalkenyl, heterocyclyl, aryl or heteroaryl ring, such as 3,5-pyrrolidinedione, maleimide, 5-norbornene-2,3-dicarboximide and phthalimide, or R$^{60}$ is aryl or heteroaryl substituted with one or more substituents selected from nitro, fluoro, chloro, and bromo, such as nitrophenyl, pentafluorophenyl and 2-bromo-pyridinium.

The term "amide" (or "amido") includes C- and N-amide groups, i.e., —C(O)NR$^{61}$R$^{62}$, and —NR$^{61}$C(O)R$^{62}$ groups, respectively. R$^{61}$ and R$^{62}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{61}$C(O)—(C$_{1-5}$ alkyl) and the group is termed "carbonylamino," and in others the amide is —NHC(O)-alkyl and the group is termed "alkanoylamino."

The term "anhydride" refers to a compound wherein two moieties R$^{40}$ and R$^{41}$ are connected with —C(O)—O—C(O)—. In some embodiments, the anhydride is a mixed anhydride, i.e., a compound wherein R$^{40}$ and R$^{41}$ are different.

The term "nitrile" or "cyano" as used herein refers to the —CN group.

Urethane groups include N- and O-urethane groups, i.e., —NR$^{63}$C(O)OR$^{64}$ and —OC(O)NR$^{63}$R$^{64}$ groups, respectively. R$^{63}$ and R$^{64}$ are independently a substituted or unsubstituted alkyl, alkenyl, alkynyl, cycloalkyl, aryl, aralkyl, heterocyclylalkyl, or heterocyclyl group as defined herein. R$^{63}$ may also be H.

The term "amine" (or "amino") as used herein refers to —NR$^{65}$R$^{66}$ groups, wherein R$^{65}$ and R$^{66}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propyl amino, isopropylamino, phenylamino, or benzylamino.

The term "sulfonamido" includes S- and N-sulfonamide groups, i.e., —SO$_2$NR$^{68}$R$^{69}$ and —NR$^{68}$SO$_2$R$^{69}$ groups, respectively. R$^{68}$ and R$^{69}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{70}$ groups, sulfoxides include —S(O)R$^{71}$ groups, sulfones include —SO$_2$R$^{72}$ groups, and sulfonyls include —SO$_2$OR$^{73}$. R$^{70}$, R$^{71}$, R$^{72}$, and R$^{73}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{74}$—C(O)—NR$^{75}$R$^{76}$ groups. R$^{74}$, R$^{75}$, and R$^{76}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{77}$)NR$^{78}$R$^{79}$ and —NR$^{77}$C(NR$^{78}$)R$^{79}$, wherein R$^{77}$, R$^{78}$, and R$^{79}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{80}$C(NR$^{81}$)NR$^{82}$R$^{83}$, wherein R$^{80}$, R$^{81}$, R$^{82}$ and R$^{83}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{84}$)=C(R$^{85}$)NR$^{86}$R$^{87}$ and —NR$^{84}$C(R$^{85}$)=C(R$^{86}$)R$^{87}$, wherein R$^{84}$, R$^{85}$, R$^{86}$ and R$^{87}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxy' as used herein can refer to —OH or its ionized form, —O$^-$.

The term "imide" refers to —C(O)NR$^{88}$C(O)R$^{89}$, wherein R$^{88}$ and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{90}$(NR$^{71}$) and —N(CR$^{90}$R$^{91}$) groups, wherein R$^{90}$ and R$^{91}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{90}$ and R$^{91}$ are not both simultaneously hydrogen.

The term "nitro" as used herein refers to an —NO$_2$ group.

The term "perhaloalkyl" as used herein refers to an alkyl group as defined above wherein every bond to hydrogen is replaced with a bond to a halogen. An example of a perhaloalkyl group is a trifluoromethyl group. The term "trifluoromethyl" as used herein refers to —CF$_3$.

The term "trifluoromethoxy" as used herein refers to —OCF$_3$.

Those of skill in the art will appreciate that compounds of the invention may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the invention encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, imidazoles may exhibit the following isomeric forms, which are referred to as tautomers of each other:

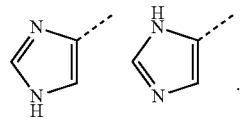

As readily understood by one skilled in the art, a wide variety of functional groups and other structures may exhibit tautomerism, and all tautomers of compounds as described herein are within the scope of the present invention.

Stereoisomers of compounds (also known as optical isomers) include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions.

Both racemic and diastereomeric mixtures, as well as the individual optical isomers can be isolated or synthesized so as to be substantially free of their enantiomeric or diastereomeric partners, and these stereoisomers are all within the scope of the invention.

The compounds of the invention may exist as solvates, especially hydrates. Hydrates may form during manufacture of the compounds or compositions comprising the compounds, or hydrates may form over time due to the hygroscopic nature of the compounds. Compounds of the invention may exist as organic solvates as well, including amide (e.g., DMF), ether, ester, ketone, nitrile, and alcohol solvates among others. The identification and preparation of any particular solvate is within the skill of the ordinary artisan of synthetic organic or medicinal chemistry.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, ornithine, homoarginine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 3rd Ed. (John Wiley & Sons, Inc., New York). Amino protecting groups include, but are not limited to, mesitylenesulfonyl (Mts), benzyloxycarbonyl (Cbz or Z), 2-chlorobenzyloxycarbonyl, t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyldimethoxybenzyloxycarbonyl (DDZ), 5-bromo-7-nitroindolinyl, and the like. Amino protecting groups susceptible to acid-mediated removal include but are not limited to Boc, TBDMS, trityl (Trt), 3,5-dimethoxyphenylisoproxycarbonyl (Ddz), 2-(4-biphenyl)isopropoxycarbonyl (Bpoc) and 2-nitrophenylsulfenyl (Nps). Amino protecting groups resistant to acid-mediated removal and susceptible to hydrogen-mediated removal include but are not limited to allyloxycarbonyl (Alloc), Cbz, nitro, and 2-chlorobenzyloxycarbonyl (2-ClCbz). Amino protecting groups resistant to acid-mediated removal and susceptible base-mediated removal include but are not limited to Fmoc, 2,7-di-tert-butyl-Fmoc, 2-fluoro-Fmoc (Fmoc(2F)), 2-(4-nitrophenylsulfonyl)ethoxycarbonyl (Nsc), (1,1-dioxobenzo [b]thiophene-2-yl)methyloxycarbonyl (Bsmoc), (1,1-dioxonaphtho[1,2-b]thiophene-2-yl)methyloxycarbonyl (a-Nsmoc), 1-(4,4-dimethyl-2,6-dioxocyclohex-1-ylidene)-3-methylbutyl (ivDde), tetrachlorophthaloyl (TCP), ethanesulfonylethoxycarbonyl (Esc), and 2-[phenyl(methyl)sulfonio]ethyloxycarbonyl tetrafluoroborate (Pms), etc. Hydroxyl protecting groups include, but are not limited to, Fmoc, TBS, photolabile protecting groups (such as nitroveratryl oxymethyl ether (Nvom)), Mom (methoxy methyl ether), and Mem (methoxyethoxy methyl ether), NPEOC (4-nitrophenethyloxycarbonyl) and NPEOM (4-nitrophenethyloxymethyloxycarbonyl). Examples and methods to synthesize the above phosphate substituted and/or sulfate substituted RPBQ compounds are disclosed in Published US Patent Application No. 20070225261A1.

As used herein, the term "coupling agent" refer to any suitable chemical useful for forming an amide bond from a primary or secondary amine and a carboxylic acid. Such coupling agents as used in any of the aspects and embodiments described herein may include, carbodiimides such as DCC, N,N'-Diisopropylcarbodiimide (DIC), N-cyclohexyl-N'-isopropylcarbodiimide (CIC), EDC or the hydrochloride salt of EDC (EDC-HCl), etc., uronium salts or aminium salts, such as HATU, HBTU, O-(benzotriazol-1-yl)-1,1,3,3-tetramethyleneuronium hexafluorophosphate (HAPyU), TATU, TBTU, O-(benzotriazol-1-yl)-1,1,3,3-pentamethyluronium hexafluorophosphate (TAPipU), O-(benzotriazol-1-yl)-N,N,N',N'-bis(pentamethylene)uronium hexafluorophosphate (HBpipU), O-(7-azabenzotrizol-1-yl)-1,3-dimethyl-1,3-trimethylene uronium hexafluorophosphate (HAMTU), O—(N-succinimidyl)-1,1,3,3-tetramethyl-uronium tetrafluoroborate (TSTU), O-(5-norbornene-2,3-dicarboximido)-N,N,N',N'-tetramethyluronium tetrafluoroborate (TNTU), O-[(ethoxycarbonyl)cyanomethylenamino]-N,N,N',N'-tetramethyluronium tetrafluoroborate (TOTU) and O-(1,2-Dihydro-2-oxo-1-pyridyl-N,N,N',N'-tetramethyluronium tetrafluoroborate (TPTU), etc., immonium salts, such as (1H-benzotriazol-1-yloxy)-N,N-dimethylmethaniminium hexachloroantimonate (BOMI), 5-(1H-benzotriazol-1-yloxy)-3,4-dihydro-1-methyl-2H-pyrrolium hexachloroantimonate (BDMP), etc., phosphonium salts, such as (benzotriazol-1-yloxy)tris(dimethylamino)phosphonium hexafluorophosphate (BOP), (benzotriazol-1-yloxy)tris(pyrrolidino)phosphonium hexafluorophosphate (PyBOP), (7-azabenzotriazol-1-yloxy)tris(di-methylamino)phosphonium hexafluorophosphate (AOP), (7-azabenzotriazol-1-yloxy)tris(pyrrolidino)phosphonium hexafluorophosphate (PyAOP), [Ethyl cyano(hydroxyimino)acetato-O2]tri-1-pyrrolidinylphosphonium hexafluorophosphate (PyOxm), etc., pentafluorophenol-based reagents such as HpyOPfp, PHySPfp, pentafluorophenyl 4-nitrobenzenesulfonate (PFNB), diphenylphosphinate (FDPP), HDMPfp, etc., phosphorus reagents, such as T3P, FMDP, 1,2-benzisoxazol-3-yl diphenyl phosphate (BIODPP), diethyl 2-(3-oxo-2,3-dihydro-1,2-benzisosulfonazolyl) phosphonate (DEBP), 4'-(4-pyridyl)-2,6-di(2-pyrazinyl)pyridine (PyDPP), etc. Representative coupling agents include, but are not limited to, (7-azabenzotriazol-1-yloxy)tripyrrolidinophosphonium hexafluorophosphate (PyAOP), O-benzotriazol-1-yl-N,N,N',N'-bis(pentamethylene)uronium hexafluorophosphate, O-(benzotriazol-1-yl)-N,N,N',N-bis(tetramethylene)uronium hexafluorophosphate, (benzotriazol-1-yloxy)dipiperidinocarbenium hexafluorophosphate, (benzotriazol-1- yloxy)tripyrrolidinophosphonium hexafluorophosphate (PyBOP), (benzotriazol-1-yloxy)tris(dimethylamino)phosphonium hexafluorophosphate (BOP), O-(benzotriazol-1-yl)-N,N,N',N'-tetramethyluronium tetrafluoroborate (TBTU), bromotripyrrolidinophosphonium hexafluorophosphate, bromotris(dimethylamino)phosphonium hexafluorophosphate, O-(6-chlorobenzotriazol-1-yl)-N,N,N',N'-tetramethyluronium tetrafluoroborate (TCTU), O-(6-chlorobenzotriazol-1-yl)-N,N,N',N'-tetramethyluronium hexafluorophosphate (HCTU), 2-chloro-1,3-dimethylimidazolidinium hexafluorophosphate, 2-chloro-1,3-dimethylimidazolidinium tetrafluoroborate, 2-chloro-1,3-dimethylimidazolidinium chloride, chlorodipyrrolidinocarbenium hexafluorophosphate, chloro-N,N,N',N'-tetramethylformamidinium hexafluorophosphate, chlorotripyrrolidinophosphonium hexafluorophosphate, (1-cyano-2-ethoxy-2-oxoethylidenaminooxy)dimethylamino-morpholino-carbenium hexafluorophosphate (COMU), dipyrrolidino(N-succinimidyloxy)carbenium hexafluorophosphate, O-[(ethoxycarbonyl)cyanomethylenamino]-N,N,N',N'-tetramethyluronium hexafluorophosphate, fluoro-N,N,N',N'-bis(tetramethylene) formamidinium hexafluorophosphate, fluoro-N,N,N',N'-bis(tetramethylene)formamidinium hexafluorophosphate, 1-hydroxybenzotriazole (HOBT), 1-hydroxy-7-azabenzotriazole (HOAT), 1-[bis(dimethylamino)methylene]-1H-1,2,3-triazolo[4,5-b]pyridinium 3-oxid hexafluorophosphate (HATU), N,N,N,N'-tetramethyl-O-(1H-benzotriazol-1-yl)uronium hexafluorophosphate (HBTU), 1-[(dimethylamino)(morpholino)methylene]-1H-[1,2,3]triazolo[4,5-b]pyridine-1-ium 3-oxide hexafluorophosphate (HDMA), O-(5-norbornene-2,3-dicarboximido)-N,N,N',N'-tetramethyluronium tetrafluoroborate, S-(1-oxido-2-pyridyl)-N,N,N,N'-tetramethylthiuronium hexafluorophosphate, O-(2-oxo-1(2H)pyridyl)-N,N,N,N'-tetramethyluronium tetrafluoroborate, N,N,N,N'-tetramethyl-O—(N-succinimidyl)uronium hexafluorophosphate, N,N'-dicyclohexylcarbodiimide (DCC), N,N'-diisopropylcarbodiimide, 1-ethyl-3-(3-dimethylaminopropyl)carbodiimide (EDC), 1-[3-(dimethylamino)propyl]-3-ethylcarbodiimide methiodide (EDC-MeI), propane phosphonic acid anhydride (T3P), N,N'-di-tert-butylcarbodiimide, N-cyclohexyl-N'-(2-morpholinoethyl)carbodiimide methyl-p-toluenesulfonate, 2-ethoxy-1-ethoxycarbonyl-1,2-dihydroquinoline, 1,1'-carbonyldiimidazole, 1,1'-carbonyldi(1,2,4-triazole), bis(4-nitrophenyl) carbonate, 4-nitrophenyl chloroformate, di(N-succinimidyl) carbonate, and 1-(2-mesitylenesulfonyl)-3-nitro-1H-1,2,4-triazole, or a combination thereof.

"Reacting" refers to bringing two or more chemical molecules into close proximity to cause or facilitate a chemical reaction of one or more of the molecules, including, e.g., a chemical reaction between the two or more chemical molecules. For example, reacting may comprise mixing and optionally continuously mixing the chemicals together. Reacting may be done by fully or partially dissolving or suspending two or more chemicals in one or more solvents, mixing a chemical in a solvent with another chemical in a solid and/or gas phase or which is attached to a solid support, such as a resin, or mixing two or more chemicals in a gas or solid phase and/or on a solid support, in accordance with procedures generally known to those skilled in the art. Reacting a compound A with a compound B also includes mixing sequentially or simultaneously compounds A, B, and C such that A reacts with compound C to form an intermediate which then reacts with compound B where the intermediate is not isolated or separated. For example, reacting an amino compound with a carboxylic acid compound to form an amide includes combining the carboxylic acid compound with a coupling agent and one or more additives (e.g., EDC and HOBT) to form an active ester in situ, which then, without isolation, reacts with an amino compound already present or subsequently added to form the amide.

"Converting" refers to the process of changing one chemical compound to another chemical compound via a chemical reaction, or changing a free acid or base of a chemical compound to a salt of the compound, or changing one salt of a chemical compound to the free acid or base of the compound or to another salt of the compound under reaction conditions capable of bringing about the change.

As used herein, an "isolated" or "purified" polypeptide or peptide is substantially free of other contaminating polypeptides such as those peptides or polypeptides from which the agent is derived, or substantially free from chemical precursors or other chemicals when chemically synthesized. For example, an isolated peptide of the present technology would be free of materials that would interfere with diagnostic or therapeutic uses of the agent. Such interfering materials may include other proteinaceous and nonproteinaceous solutes.

As used herein, the term "net charge" refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. In one aspect, peptides (as disclosed herein) also include all stereoisomers and geometric isomers of the peptides, including diastereomers, enantiomers, and cis/trans (E/Z) isomers. In some embodiments, the amino acids of the peptides are D amino acids.

As used herein, the term "small molecule" includes organic compounds, organometallic compounds, salts of organic and organometallic compounds, monosaccharides, amino acids, and nucleotides. Small molecules can further include molecules that would otherwise be considered biological molecules, except their molecular weight is not greater than 1,000. Thus, small molecules may be lipids, oligosaccharides, oligopeptides, and oligonucleotides, and their derivatives, having a molecular weight of 1,000 or less.

Methods of the Present Technology

In one aspect, a process is provided for synthesizing the compounds of the present technology. In some embodiments, the process is directed at producing one or more of the intermediates as the end product; in some embodiments, the process is directed at producing the compounds of the present technology as the end product of the process. Each embodiment may be performed independently of any other embodiment, or in combination with other embodiments. In any of the embodiments, it may be that the process is a solution phase process and not a solid phase process. In any of the embodiments, it may be that the purity of the product of the process is at least about 95% as determined by high performance liquid chromatography (HPLC). The purity may be about 98.2%, about 98.4%, about 98.6%, about 98.8%, about 99.0%, about 99.2%, about 99.4%, about 99.6%, about 99.8%, or any range including and between any two of these values or greater than any one of these values. In any of the embodiments, it may be that the product of the process may be at least about 98.0% pure as determined by gas chromatographic analysis. The purity may be about 98.2%, about 98.4%, about 98.6%, about 98.8%, about 99.0%, about 99.2%, about 99.4%, about 99.6%, about 99.8%, or any range including and between any two of these values or greater than any one of these values. In any of the embodiments, it may be the product has less than about 50 ppm heavy metals. The heavy metals may be about 45 ppm, about 40 ppm, about 35 ppm, about 30 ppm, about 25 ppm, about 20 ppm, about 15 ppm, about 10 ppm, about 5 ppm, about 1 ppm, or any range in between and including any two of these values or lower than any one of these values.

Surprisingly, the processes of this technology described herein provide the compound of formula VIII or a salt thereof in high purity without the need for purification by column chromatography methods.

In an aspect, a process is provided for the preparation of a compound of formula VIII or a salt thereof:

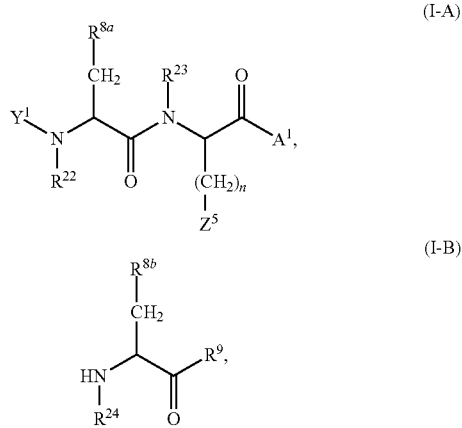

(VIII)

the method comprising reacting a compound of formula I-A or a salt thereof with a compound of formula I-B or a salt thereof:

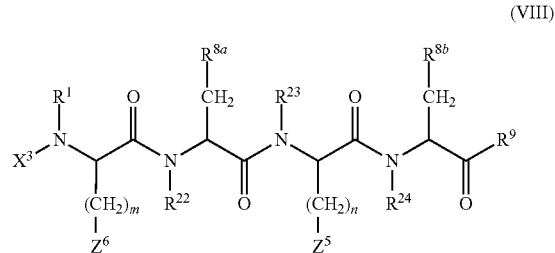

(I-A)

(I-B)

to form a compound of formula I-C or a salt thereof:

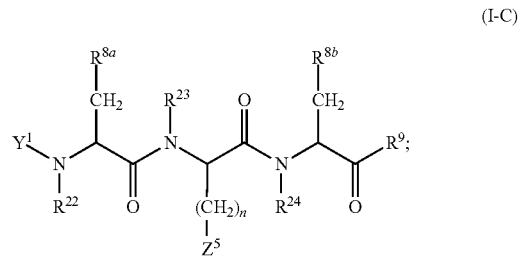

(I-C)

converting the compound of formula I-C or a salt thereof to a compound of formula I-D or a salt thereof:

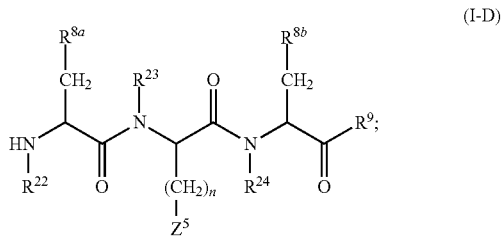

(I-D)

reacting the compound of formula I-D or a salt thereof with a compound of formula I-E or a salt thereof to form the compound of formula VIII or a salt thereof:

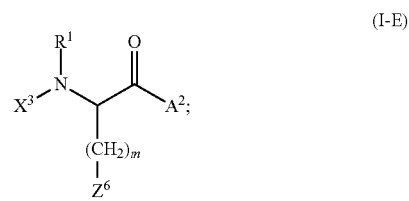

(I-E)

wherein
$A^1$ and $A^2$ each independently, together with the carbonyl group to which each is attached, forms a carboxylic acid, active ester, anhydride, or acid halide, for example, $A^1$ and $A^2$ are each independently —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group;
$R^1$ and $R^2$ are each independently
(i) hydrogen;
(ii) substituted or unsubstituted $C_1$-$C_6$ alkyl;
(iii) substituted or unsubstituted aralkyl;
(iv) substituted or unsubstituted $C_3$-$C_8$ cycloalkyl or cycloalkylalkyl;
(v) substituted or unsubstituted $C_2$-$C_6$ alkenyl;
(vi) an amino protecting group;
or $R^1$ and $R^2$ together form a 3, 4, 5, 6, 7, or 8 membered substituted or unsubstituted heterocyclyl or heteroaryl group;

$R^{8a}$ and $R^{8b}$ are each independently selected from

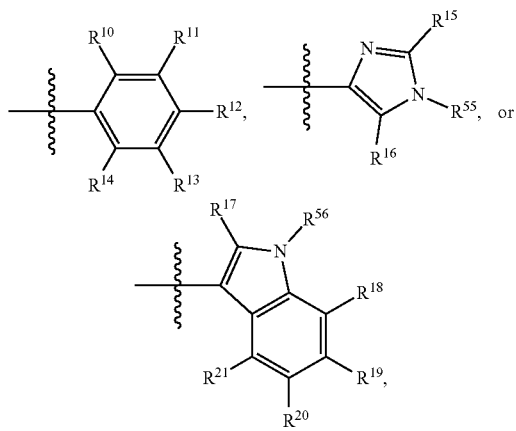

where $R^{10}$, $R^{11}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R"; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R" is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{12}$ is selected from hydrogen, —OH, halogen (e.g., F, Cl, Br, I), $C_1$-$C_6$ alkyl, —O—$C_1$-$C_6$ alkyl, —NH—$C_1$-$C_6$ alkyl, —N($C_1$-$C_6$ aralkyl), —O-aralkyl, —NH-aralkyl, —N(aralkyl)$_2$, —N($C_1$-$C_6$ alkyl)(aralkyl), —C(O)-alkyl, —C(O)-aryl, or —C(O)-aralkyl, wherein each alkyl, aryl or aralkyl group is substituted or unsubstituted;

$R^{22}$, $R^{23}$, and $R^{24}$ are each independently hydrogen or a $C_1$-$C_4$ alkyl;

n is 1, 2, 3, 4, or 5;

m is 1, 2, 3, 4, or 5;

$X^1$, $X^2$ and $X^4$ are independently at each occurrence hydrogen or an amino protecting group, such as an amino protecting group susceptible to acid-mediated removal or an amino protecting group resistant to acid-mediated removal and susceptible to base-mediated or hydrogen-mediated removal;

$X^3$ is $R^2$, hydrogen or an amino protecting group;

$Y^1$ is an amino protecting group, such as an amino protecting group susceptible to acid-mediated removal or an amino protecting group resistant to acid-mediated removal and susceptible to base-mediated or hydrogen-mediated removal;

$Z^5$ and $Z^6$ are each independently —NHX$^1$, —C(N—X$^4$)—NH—X$^2$, —NX$^1$C(N—X$^4$)—NH—X$^2$, —NX$^1$($C_1$-$C_6$ alkyl), —NX$^1$($C_6$-$C_{10}$ aryl), —NX$^1$($C_7$-$C_{12}$ aralkyl), or nitrogen-containing heterocyclyl or heteroaryl group wherein each alkyl, aryl, aralkyl, heterocyclyl, or heteroaryl group is substituted or unsubstituted.

In an aspect, a process is provided for the preparation of a compound of formula VIII or a salt thereof:

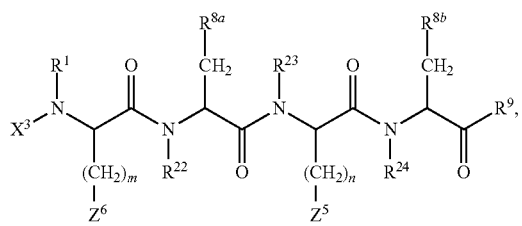

(VIII)

the method comprising reacting a compound of formula II-A or a salt thereof with a compound of formula I-E or a salt thereof:

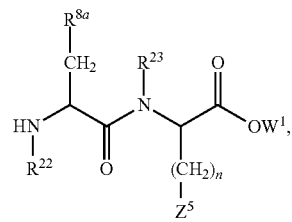

(II-A)

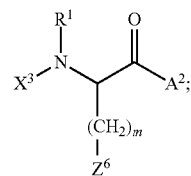

(I-E)

to form a compound of formula II-C or a salt thereof:

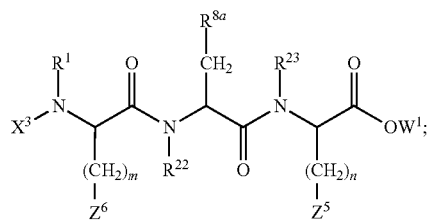

(II-C)

converting the compound of formula II-C or a salt thereof to a compound of formula II-D or a salt thereof:

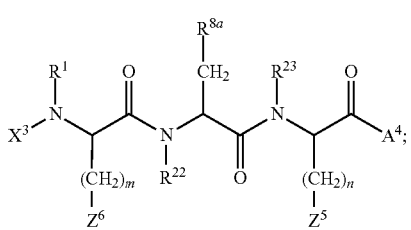

(II-D)

reacting the compound of formula II-D or a salt thereof with a compound of formula I-B or a salt thereof to form the compound of formula VIII or a salt thereof:

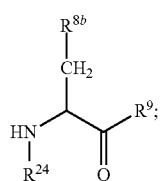

(I-B)

wherein $A^2$ and $A^4$ each independently, together with the carbonyl group to which each is attached, forms a carboxylic acid, active ester, anhydride, or acid halide, for example, $A^2$ and $A^4$ are each independently OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^1$ and $R^2$ are each independently (i) hydrogen;

(ii) substituted or unsubstituted $C_1$-$C_6$ alkyl;

(iii) substituted or unsubstituted aralkyl;

(iv) substituted or unsubstituted $C_3$-$C_8$ cycloalkyl or cycloalkylalkyl;

(v) substituted or unsubstituted $C_2$-$C_6$ alkenyl;

(vi) an amino protecting group;

or $R^1$ and $R^2$ together form a 3, 4, 5, 6, 7, or 8 membered substituted or unsubstituted heterocyclyl or heteroaryl group;

$R^{8a}$ and $R^{8b}$ are each independently selected from

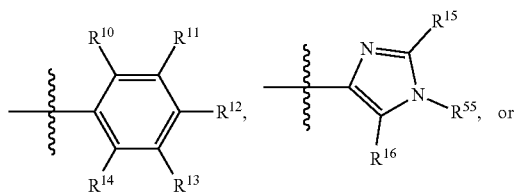

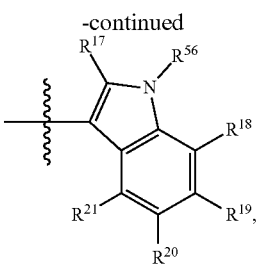

where $R^{10}$, $R^{11}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R"; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R" is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{12}$ is selected from hydrogen, —OH, halogen (e.g., F, Cl, Br, I), $C_1$-$C_6$ alkyl, —O—$C_1$-$C_6$ alkyl, —NH—$C_1$-$C_6$ alkyl, —N($C_1$-$C_6$ aralkyl, —O-aralkyl, —NH-aralkyl, —N(aralkyl)$_2$, —N($C_1$-$C_6$ alkyl)(aralkyl), —C(O)-alkyl, —C(O)-aryl, or —C(O)-aralkyl, wherein each alkyl, aryl or aralkyl group is substituted or unsubstituted;

$R^{22}$, $R^{23}$, and $R^{24}$ are each independently hydrogen or a $C_1$-$C_4$ alkyl;

n is 1, 2, 3, 4, or 5;

m is 1, 2, 3, 4, or 5;

$W^1$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$X^1$, $X^2$ and $X^4$ are independently at each occurrence hydrogen or an amino protecting group, such as an amino protecting group resistant to acid-mediated removal and susceptible to base-mediated or hydrogen-mediated removal;

$X^3$ is $R^2$, hydrogen or an amino protecting group; and $Z^5$ and $Z^6$ are each independently —NHX$^1$, —C(N—X$^4$)—NH—X$^2$, —NX$^1$C(N—X$^4$)—NH—X$^2$, —NX$^1$($C_1$-$C_6$ alkyl), —NX$^1$($C_6$-$C_{10}$ aryl), —NX$^1$($C_7$-$C_{12}$ aralkyl), or nitrogen-containing heterocyclyl or heteroaryl group wherein each alkyl, aryl, aralkyl, heterocyclyl, or heteroaryl group is substituted or unsubstituted.

In some aspects, the compound of formula I-A or a salt thereof is prepared by coverting a compound of I-F or a salt thereof:

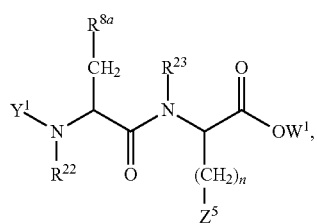

(I-F)

to the compound of I-A, wherein n, $W^1$, $Y^1$, $Z^5$, $R^{22}$, $R^{23}$, and $R^{8a}$ are as defined herein.

In some aspects, coverting a compound of I-F or a salt thereof to the compound of I-A or a salt thereof includes converting the group $OW^1$ in the compound of formula I-F or a salt thereof to OH under hydrolysis conditions to form a compound of formula I-A or a salt thereof wherein $A^1$ is OH. In some aspects, the compound of formula I-A or a salt thereof wherein $A^1$ is OH is further converted to an anhydride (e.g., mixed anhydride), such as a compound of formula I-A or a salt thereof wherein $A^1$ is —OC(O)—$R^{59}$ by a method comprising reacting the compound of formula I-A or a salt thereof wherein $A^1$ is OH with ClC(O)—$R^{59}$. In some aspects, the compound of formula I-A or a salt thereof wherein $A^1$ is OH is further converted to a compound of formula I-A or a salt thereof wherein $A^1$ is F by a method comprising reacting the compound of formula I-A or a salt thereof wherein $A^1$ is OH with a fluorinating agent such as cyanuric fluoride, diethylaminosulfur trifluoride, tetramethylfluoroformamidinium hexafluorophosphate (TFFH), and fluoro-dipyrrolidinocarbenium hexafluorophosphate (BTFFH). In some aspects, the compound of formula I-A or a salt thereof wherein $A^1$ is OH is further converted to a compound of formula I-A or a salt thereof wherein $A^1$ is Cl by a method comprising reacting the compound of formula I-A or a salt thereof wherein $A^1$ is OH with a chlorinating agent such as phosphorus pentachloride, oxalyl chloride or thionyl chloride. In some aspects, the compound of formula I-A or a salt thereof wherein $A^1$ is OH is further converted to a compound of formula I-A or a salt thereof wherein $A^1$ is Br by a method comprising reacting the compound of formula I-A or a salt thereof wherein $A^1$ is OH with a brominating agent such as phosphorus tribromide. In some aspects, the compound of formula I-A or a salt thereof wherein $A^1$ is OH is further converted to an active ester, such as a compound of formula I-A or a salt thereof wherein $A^1$ is —O—$R^{58}$, by a method comprising reacting the compound of formula I-A or a salt thereof wherein $A^1$ is OH with $Lv^1$-$R^{58}$, wherein $Lv^1$ is a leaving group. Examples of $Lv^1$-$R^{58}$ include acrylic acid N-hydroxysuccinimide ester, bis(4-nitrophenyl)carbonate, bis(4-nitrophenyl)carbonate, bis(pentafluorophenyl)carbonate, 2-bromo-1-ethyl-pyridinium tetrafluoroborate, N,O-dimethylhydroxylamine, N,N'-disuccinimidyl carbonate, ethyl (hydroxyimino)cyanoacetate, 1-hydroxybenzotriazole hydrate, N-hydroxymaleimide, N-hydroxy-5-norbornene-2,3-dicarboxylic acid imide, 3-(4-hydroxyphenyl)propionic acid N-hydroxysuccinimide ester, N-hydroxyphthalimide, N-hydroxysuccinimide, N-hydroxysuccinimidyl acetoacetate, N-hydroxysulfosuccinimide, iodoacetic acid N-hydroxysuccinimide ester, 4-nitrobenzyl chloroformate, 4-nitrophenyl chloroformate, pentafluorophenyl trifluoroacetate, phenoxyacetic acid N-hydroxysuccinimide ester, and N-succinimidyl N-methylcarbamate.

In some aspects, $A^1$ is OH.

In some aspects, the compound of formula II-A or a salt thereof is prepared by coverting a compound of I-F or a salt thereof to the compound of II-A or a salt thereof.

In some aspects, $A^2$ is OH. In some aspects, the compound of I-E is an active ester, such as a compound wherein $A^2$ is —O—$R^{58}$ and is prepared by a method comprising reacting the compound of formula I-E or a salt thereof wherein $A^2$ is OH with $Lv^1$-$Re^{58}$ as described herein. In some aspects, the compound of I-E or a salt thereof is an anhydride (e.g., mixed anhydride), such as a compound wherein $A^2$ is —OC(O)—$R^{59}$ and is prepared by a method comprising reacting the compound of formula I-E or a salt thereof wherein $A^2$ is OH with ClC(O)—$R^{59}$. In some aspects, the compound of formula I-E wherein $A^2$ is F is prepared by a method comprising reacting the compound of formula I-E or a salt thereof wherein $A^2$ is OH with a fluorinating agent such as cyanuric fluoride, diethylaminosulfur trifluoride, tetramethylfluoroformamidinium hexafluorophosphate (TFFH), and fluoro-dipyrrolidinocarbenium hexafluorophosphate (BTFFH). In some aspects, the compound of formula I-E or a salt thereof wherein $A^2$ is Cl is prepared by a method comprising reacting the compound of formula I-E or a salt thereof wherein $A^2$ is OH with a chlorinating agent such as phosphorus pentachloride, oxalyl chloride or thionyl chloride. In some aspects, the compound of formula I-E or a salt thereof wherein $A^2$ is Br is prepared by a method comprising reacting the compound of formula I-E or a salt thereof wherein $A^2$ is OH with a brominating agent such as phosphorus tribromide.

In some aspects, the compound of formula of I-F or a salt thereof is prepared by a method comprising reacting a compound of formula I-G or a salt thereof with a compound of formula I-H or a salt thereof:

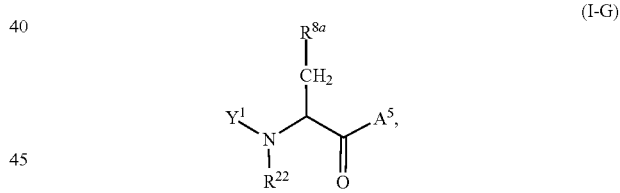

(I-G)

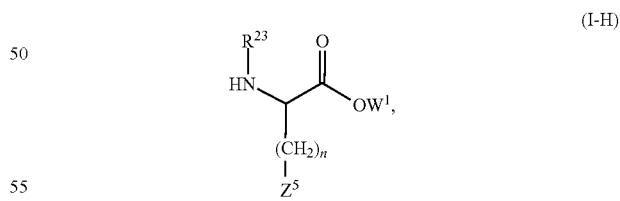

(I-H)

wherein $R^{8a}$, $R^{22}$, $R^{23}$, $W^1$, $Y^1$, $Z^5$ and n are as defined herein, and $A^5$ together with the carbonyl group to which it is attached forms a carboxylic acid, active ester, anhydride, or acid halide, for example, $A^5$ may be OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group. In some aspects, $A^5$ is OH.

In another aspect, a process is provided for the preparation of a compound of formula VIII or a salt thereof:

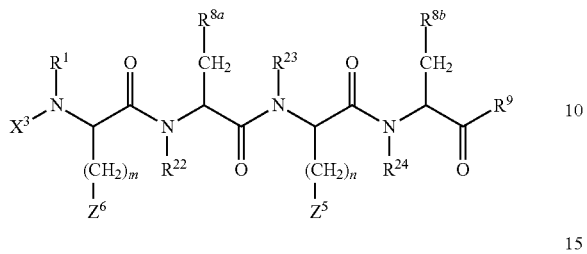

(VIII)

the method comprising reacting a compound of formula III-A or a salt thereof with a compound of formula III-B or a salt thereof to form a compound of formula VIII or a salt thereof:

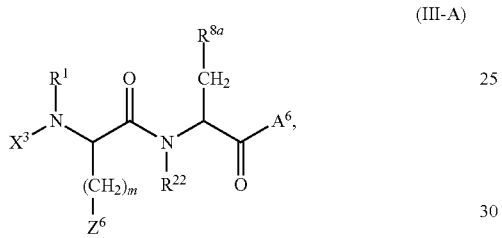

(III-A)

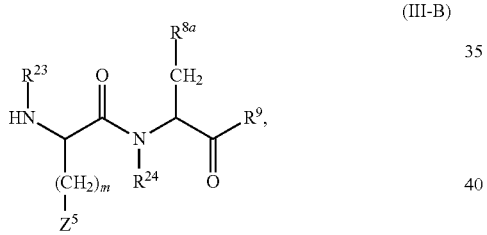

(III-B)

wherein
- $A^6$ together with the carbonyl group to which it is attached forms a carboxylic acid, active ester, anhydride, or acid halide, for example, $A^6$ is —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group;
- $R^1$ and $R^2$ are each independently
  - (i) hydrogen;
  - (ii) substituted or unsubstituted $C_1$-$C_6$ alkyl;
  - (iii) substituted or unsubstituted aralkyl;
  - (iv) substituted or unsubstituted $C_3$-$C_8$ cycloalkyl or cycloalkylalkyl;
  - (v) substituted or unsubstituted $C_2$-$C_6$ alkenyl;
  - (vi) an amino protecting group;

or $R^1$ and $R^2$ together form a 3, 4, 5, 6, 7, or 8 membered substituted or unsubstituted heterocyclyl or heteroaryl group;

$R^{8a}$ and $R^{8b}$ are each independently selected from

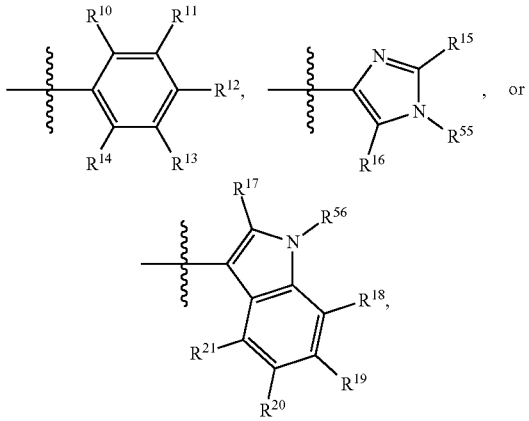

, or where $R^{10}$, $R^{11}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, $C_1$-$C_4$ dialkyl amino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R"; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R" is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{12}$ is selected from hydrogen, —OH, halogen (e.g., F, Cl, Br, I), $C_1$-$C_6$ alkyl, —O—$C_1$-$C_6$ alkyl, —NH—$C_1$-$C_6$ alkyl, —N($C_1$-$C_6$ alkyl)$_2$, $C_1$-$C_4$-perhaloalkyl, aralkyl, —O-aralkyl, —NH-aralkyl, —N(aralkyl)$_2$, —N($C_1$-$C_6$ alkyl)(aralkyl), —C(O)-alkyl, —C(O)-aryl, or —C(O)-aralkyl, wherein each alkyl, aryl or aralkyl group is substituted or unsubstituted;

$R^{22}$, $R^{23}$, and $R^{24}$ are each independently hydrogen or a $C_1$-$C_4$ alkyl;

n is 1, 2, 3, 4, or 5;

m is 1, 2, 3, 4, or 5;

$X^1$, $X^2$ and $X^4$ are independently at each occurrence hydrogen or an amino protecting group, such as an amino protecting group susceptible to acid-mediated removal or an amino protecting group resistant to acid-mediated removal and susceptible to base-mediated or hydrogen-mediated removal;

$X^3$ is $R^2$, hydrogen or an amino protecting group; and $Z^5$ and $Z^6$ are each independently —NHX$^1$, —C(N—X$^4$)—NH—X$^2$, —NX$^1$C(N—X$^4$)—NH—X$^2$, —NX$^1$($C_1$-$C_6$ alkyl), —NX$^1$($C_6$-$C_{10}$ aryl), —NX$^1$($C_7$-$C_{12}$ aralkyl), or nitrogen-containing heterocyclyl or heteroaryl group wherein each alkyl, aryl, aralkyl, heterocyclyl, or heteroaryl group is substituted or unsubstituted.

In some aspects, the compound of formula III-A or a salt thereof is prepared by a method comprising converting the compound of formula III-C or a salt thereof to a compound of formula III-A or a salt thereof:

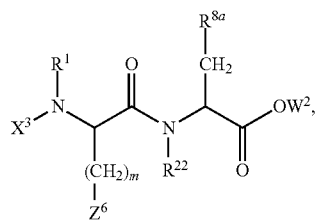

(III-C)

wherein m, $X^1$, $X^3$, $Z^6$, $R^{22}$, $R^1$, and $R^{8a}$ are as defined herein, and $W^2$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In some aspects, converting a compound of formula III-C or a salt thereof to the compound of III-A or a salt thereof comprises converting the $OW^2$ group in the compound of formula III-C to OH under hydrolysis conditions to form a compound of formula III-A or a salt thereof wherein $A^6$ is OH. In some aspects, the compound of formula III-A or a salt thereof wherein $A^6$ is OH is further converted to an anhydride (e.g., mixed anhydride), such as a compound of formula III-A or a salt thereof wherein $A^6$ is —OC(O)—$R^{59}$ by a method comprising reacting the compound of formula III-A or a salt thereof wherein $A^6$ is OH with ClC(O)—$R^{59}$. In some aspects, the compound of formula III-A or a salt thereof wherein $A^6$ is OH is further converted to an active ester (e.g., $A^6$ is —O—$R^{58}$) by a method comprising reacting the compound of formula III-A or a salt thereof wherein $A^6$ is OH with $Lv^1$-$R^{58}$ as described herein. In some aspects, the compound of formula III-A or a salt thereof wherein $A^6$ is OH is further converted to a compound of formula III-A or a salt thereof wherein $A^6$ is F by a method comprising reacting the compound of formula III-A or a salt thereof wherein $A^6$ is OH with a fluorinating agent such as cyanuric fluoride, diethylaminosulfur trifluoride, tetramethylfluoroformamidinium hexafluorophosphate (TFFH), and fluorodipyrrolidinocarbenium hexafluorophosphate (BTFFH). In some aspects, the compound of formula III-A or a salt thereof wherein $A^6$ is OH is further converted to a compound of formula III-A or a salt thereof wherein $A^6$ is Cl by a method comprising reacting the compound of formula III-A or a salt thereof wherein $A^6$ is OH with a chlorinating agent such as phosphorus pentachloride, oxalyl chloride or thionyl chloride. In some aspects, the compound of formula III-A or a salt thereof wherein $A^6$ is OH is further converted to a compound of formula III-A or a salt thereof wherein $A^6$ is Br by a method comprising reacting the compound of formula III-A or a salt thereof wherein $A^6$ is OH with a brominating agent such as phosphorus tribromide.

In some aspects, $A^6$ is OH.

In some aspects, the compound of formula III-C or a salt thereof is prepared by a method comprising reacting a compound of formula III-D or a salt thereof with a compound of formula I-E to form a compound of formula III-C or a salt thereof:

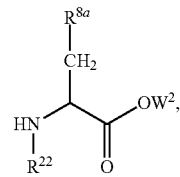

(III-D)

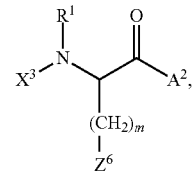

(I-E)

wherein m, $W^2$, $X^1$, $X^3$, $Z^6$, $R^{22}$, $R^1$, and $R^{8a}$ are as defined herein, and $A^2$ together with the carbonyl group to which it is attached forms a carboxylic acid, active ester, anhydride, or acid halide, for example, $A^2$ is —OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroarylalkyl, heterocyclyl, or heterocyclylalkyl group. In some embodiments, $A^2$ is OH.

In some aspects, the compound of formula III-B or a salt thereof is prepared by a method comprising converting a compound of formula III-E or a salt thereof to the compound of formula III-B or a salt thereof:

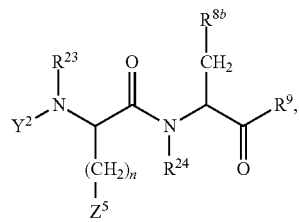

(III-E)

wherein $Y^2$ is an amino protecting group, such as an amino protecting group susceptible to acid-mediated removal or an amino protecting group resistant to acid-mediated removal and susceptible to base-mediated or hydrogen-mediated removal, and n, $Z^5$, $R^{23}$, $R^{24}$, $R^{8b}$, and $R^9$ are as defined herein.

In some aspects, the compound of formula III-E or a salt thereof is prepared by a method comprising reacting a compound of formula I-B or a salt thereof with a compound of formula III-F or a salt thereof to form a compound of formula III-E or a salt thereof:

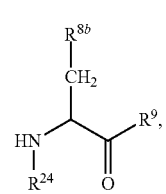

(I-B)

-continued

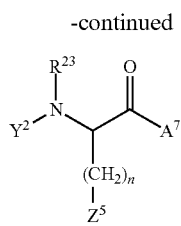
(III-F)

wherein $R^{8b}$, $R^9$, $R^{23}$, $R^{24}$, $Y^2$, $Z^5$ and n are as defined above, and $A^7$ together with the carbonyl group to which it is attached forms a carboxylic acid, active ester, anhydride, or acid halide, for example, $A^7$ is OH, —O—$R^{58}$, —OC(O)—$R^{59}$, F, Cl, or Br, $R^{58}$ is a substituted or unsubstituted aryl, heteroaryl, or heterocyclyl group, and $R^{59}$ is a substituted or unsubstituted alkyl, alkenyl, cycloalkyl, cycloalkylalkyl, aryl, aralkyl, heteroaryl, heteroaryl alkyl, heterocyclyl, or heterocyclylalkyl group. In some embodiments, $A^7$ is OH.

Hydrolysis conditions may comprise an aqueous solution of an alkali metal hydroxide (e.g., LiOH, NaOH or KOH) or an alkaline earth metal hydroxide (e.g., Ca(OH)$_2$ or Mg(OH)$_2$). The solution may further comprise an organic solvent, for example, a water miscible or partially miscible organic solvent, such as $CH_3OH$, EtOH, DMF, DMA, $CH_3CN$, acetone, dioxane, THF, or a mixture thereof.

In some embodiments, $W^1$ or $W^2$ is benzyl and —$OW^1$ or —$OW^2$ is converted to OH by a method comprising a hydrogen source and a transition metal catalyst as described herein. For example, $H_2$ and a supported catalyst such as Pd or Pt on carbon may be used to convert (reductively cleave) the benzyl to H.

In some embodiments, $W^1$ or $W^2$ is tert-butyl and —$OW^1$ or —$OW^2$ is converted to OH by a method comprising a cleaving acid as described herein.

In some embodiments of any of the aspects, if $Y^1$ or $Y^2$ is an amino protecting group susceptible to acid-mediated removal, then none of $X^1$, $X^2$, $X^3$ and $X^4$ is an amino protecting group susceptible to acid-mediated removal. In some embodiments of any of the above aspects, if one of $X^1$, $X^2$, $X^3$ and $X^4$ is an amino protecting group susceptible to acid-mediated removal, then neither $Y^1$ nor $Y^2$ is an amino protecting group susceptible to acid-mediated removal. In some embodiments of any of the above aspects, if one of $X^1$, $X^2$, $X^3$ and $X^4$ is an amino protecting group susceptible to acid-mediated removal, then all of the remaining $X^1$, $X^2$, $X^3$ and $X^4$ are hydrogen or an amino protecting group susceptible to acid-mediated removal, and neither $Y^1$ nor $Y^2$ is an amino protecting group susceptible to acid-mediated removal.

In some embodiments of any of the aspects, $Y^1$ is an amino protecting group resistant to acid-mediated removal and susceptible to hydrogen-mediated removal. In some embodiments $Y^2$ is an amino protecting group resistant to acid-mediated removal and susceptible to hydrogen-mediated removal. For example, $Y^1$ or $Y^2$ may independently be Cbz, and $H_2$ and a supported catalyst such as Pd or Pt on carbon may be used to convert (reductively cleave) the Cbz to H. In some embodiments at least one of $X^1$, $X^2$, $X^3$ and $X^4$ is an amino protecting group susceptible to acid-mediated removal. In some embodiments $X^3$ and at least one of $X^1$, $X^2$ and $X^4$ are independently an amino protecting group susceptible to acid-mediated removal. In other embodiments, $X^3$ and at least two of $X^1$, $X^2$ and $X^4$ are independently an amino protecting group susceptible to acid-mediated removal.

In any of the embodiments, it may be that $Y^1$ and $Y^2$ are independently allyloxycarbonyl (Alloc), 2-chlorobenzyloxycarbonyl (2-ClCbz), or benzyloxycarbonyl (Cbz); and each of $X^1$, $X^2$ and $X^4$ at each occurrence is independently hydrogen or tert-butyloxycarbonyl (Boc), trityl (Trt), 3,5-dimethoxyphenylisoproxycarbonyl (Ddz), 2-(4-biphenyl) isopropoxycarbonyl (Bpoc) or 2-nitrophenylsulfenyl (Nps). In any of the embodiments, it may be that $Y^1$ and $Y^2$ are independently Boc, Trt, Ddz, Bpoc, or Nps, and each of $X^1$, $X^2$ and $X^4$ at each occurrence is independently hydrogen, Alloc, Cbz or 2-ClCbz.

In some embodiments of any of the aspects, $Y^1$ is an amino protecting group susceptible to acid-mediated removal. In some embodiments $Y^2$ is an amino protecting group susceptible to acid-mediated removal. In some embodiments at least one of $X^1$, $X^2$, $X^3$ and $X^4$ is an amino protecting group resistant to acid-mediated removal and susceptible to hydrogen-mediated removal. In some embodiments $X^3$ and at least one of $X^1$, $X^2$ and $X^4$ are independently an amino protecting group resistant to acid-mediated removal and susceptible to hydrogen-mediated removal. In other embodiments, $X^3$ and at least two of $X^1$, $X^2$ and $X^4$ are independently an amino protecting group resistant to acid-mediated removal and susceptible to hydrogen-mediated removal.

In any of the embodiments, it may be that $Y^1$ and $Y^2$ are Boc, Trt, Ddz, Bpoc or Nps; $X^1$ at each occurrence is independently hydrogen, Alloc, Cbz, or 2-ClCbz; $X^2$ at each occurrence is independently hydrogen, Alloc, Cbz, or 2-ClCbz; and $X^4$ at each occurrence is independently hydrogen, nitro, Alloc, Cbz, or 2-ClCbz.

In any of the embodiments, it may be that $Y^1$ and/or $Y^2$ are independently an amino protecting group susceptible to acid-mediated removal. In any of the embodiments, $X^1$, $X^2$ and/or $X^4$ at each occurrence is independently an amino protecting group resistant to acid-mediated removal and susceptible to base-mediated or hydrogen-mediated removal. In any of the embodiments, it may be that $Y^1$ and/or $Y^2$ are Boc; $X^1$ at each occurrence is independently hydrogen, Alloc, Cbz, or 2-ClCbz; $X^2$ at each occurrence is independently hydrogen, Alloc, Cbz, or 2-ClCbz; and $X^4$ at each occurrence is independently hydrogen, nitro, Alloc, Cbz, or 2-ClCbz. In some embodiments, when $Z^5$ is —C(NH)—NH—$X^2$, $X^1$ is hydrogen. In some embodiments, when $Z^5$ is —C(N—$X^4$)—NH—$X^2$, $X^1$ is hydrogen and at least one of $X^2$ and $X^4$ is not H. In any of the embodiments, it may be that when $X^2$ is an amino protecting group resistant to acid-mediated removal and susceptible to hydrogen-mediated removal, $X^1$ is hydrogen. In any of the embodiments, it may be that when $X^1$ is an amino protecting group resistant to acid-mediated removal and susceptible to hydrogen-mediated removal, $X^2$ is hydrogen.

In any of the embodiments, it may be that $Y^1$ and/or $Y^2$ are independently an amino protecting group resistant to acid-mediated removal and susceptible to base-mediated removal. In any of the embodiments, it may be that $Y^1$ and/or $Y^2$ are Fmoc. In any of the embodiments, it may be that $Y^1$ and/or $Y^2$ are independently an amino protecting group resistant to acid-mediated removal and susceptible to hydrogen-mediated removal. In any of the embodiments, $X^1$, $X^2$ and/or $X^4$ at each occurrence independently may be an amino protecting group susceptible to acid-mediated removal. In any of the embodiments, it may be that $Y^1$ and/or $Y^2$ are independently Alloc, Cbz, or 2-ClCbz; $X^1$, $X^2$ and/or $X^4$ at each occurrence is independently hydrogen or Boc. In any of the aspects or embodiments, $Z^5$ and $Z^6$ may each be independently —$NHX^1$, —C(N—$X^4$)—NH—$X^2$, —$NX^1C$ (N—X⁴)—NH—X², or substituted or unsubstituted imidazolyl or indolyl or other substituted or unsubstituted nitrogen-containing heterocycles and heteroaromatic groups as described herein, including without limitation, substituted and unsubstituted pyrrolyl, pyrrolidinyl, pyrrolinyl, imidazolidinyl, thiazolyl, pyrazinyl, pyridinyl, triazolyl, tetrazolyl, piperidinyl, peiperazinyl, morpholinyl, benzimidazolyl, azaindolyl, indazolyl, imidazopyridinyl, pyrazolopyridinyl, and triazolopyridinyl. In some embodiments, when $Z^5$ is —NX¹C(N—X⁴)—NH—X² or —C(NH)—NH—X², $X^1$ is hydrogen. In some embodiments, when $Z^5$ is —NX¹C(N—X⁴)—NH—X², $X^1$ is hydrogen and at least one of $X^2$ and $X^4$ is not H. In any of the embodiments, it may be that when $X^2$ is an amino protecting group susceptible to acid-mediated removal, $X^1$ is hydrogen. In any of the embodiments, it may be that when $X^1$ is an amino protecting group susceptible to acid-mediated removal, $X^2$ is hydrogen.

In any of the embodiments, it may be that $X^3$ is an amino protecting group susceptible to acid-mediated removal. In some embodiments $X^3$ is an amino protecting group susceptible to acid-mediated removal, such as, but not limited to Boc, Trt, Ddz, Bpoc, or Nps. In any of the aspects, it may be that $Z^5$ is —NHX¹ and $Z^6$ is —NX¹C(N—X⁴)—NH—X². In some such embodiments, $X^1$ is H and in others, $X^1$, $X^2$ and $X^4$ are H. In some embodiments, $Z^5$ is —NHBoc and $Z^6$ is —NHC(NH)—NH₂. In certain embodiments, in is 3 and n is 4.

In any of the embodiments, it may be that $R^{8a}$ or $R^{8b}$ is

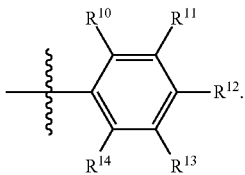

In some such embodiments, $R^{10}$, $R^{11}$, $R^{12}$, $R^{13}$, and $R^{14}$ are all hydrogen; in other such embodiments, $R^{10}$ and $R^{14}$ may be methyl and $R^{12}$ may be —OH. In any of the above embodiments, it may be that $R^9$ is NH₂. In any of the above embodiments, it may be that $Z^5$ or $Z^6$ is —NH₂ or —NHC(NH)NH₂, and n or m is 3 or 4. In any of the above embodiments, it may be that one of $R^{8a}$ and $R^{8b}$ is

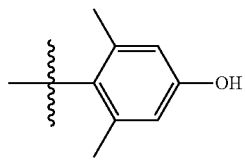 [SMILES: *c1c(C)cc(O)cc1C]

and one is

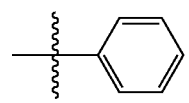

where $R^9$ is —NH₂; $Z^5$ is —NH₂; and n is 3 or 4.

In any of the embodiments, it may be that $R^9$ is NR'R". In any of the above embodiments, it may be that $R^9$ is NH₂. In any of the above embodiments other than in the compound of formula I or a salt thereof, it may be that $R^9$ is OR' and R' is not hydrogen. In some embodiments of the compound of formula I or a salt thereof, it may be that $R^9$ is OH.

In any of the embodiments, it may be that all of $R^{22}$, $R^{23}$, and $R^{24}$ are hydrogen. In any of the embodiments, it may be that $R^{22}$ and $R^{23}$ are hydrogen, and $R^{24}$ is $C_1$-$C_4$ alkyl, such as methyl. In any of the embodiments, it may be that $R^{22}$ and $R^{24}$ are hydrogen, and $R^{25}$ is $C_1$-$C_4$ alkyl, such as methyl. In any of the embodiments, it may be that $R^{23}$ and $R^{24}$ are hydrogen, and $R^{22}$ is $C_1$-$C_4$ alkyl, such as methyl. In any of the embodiments, it may be that $R^{22}$ and $R^{23}$ are $C_1$-$C_4$ alkyl, such as methyl, and $R^{24}$ is hydrogen. In any of the embodiments, it may be that $R^{22}$ and $R^{24}$ are $C_1$-$C_4$ alkyl, such as methyl, and $R^{25}$ is hydrogen. In any of the embodiments, it may be that $R^{23}$ and $R^{24}$ are $C_1$-$C_4$ alkyl, such as methyl, and $R^{22}$ is hydrogen. In any of the embodiments, it may be that all of $R^{22}$, $R^{23}$, and $R^{24}$ are $C_1$-$C_4$ alkyl, such as methyl.

In certain embodiments the the present methods, the compound of formula VIII or a salt thereof is a compound of formula VIII-B or a salt thereof wherein $R^1$ is hydrogen; $X^3$ is an amino protecting group susceptible to acid-mediated removal; $Z^5$ and $Z^6$ are independently selected from —NHX¹ or —NHC(NH)—NH₂, $X^1$ is an amino protecting group susceptible to acid-mediated removal; m and n are independently selected from 2, 3, or 4; $R^9$ is NH₂, $R^{8a}$ and $R^{8b}$ are independently

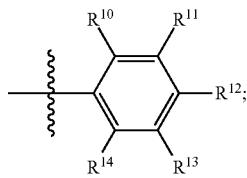

$R^{10}$ and $R^{14}$ at each occurrence are independently selected from hydrogen or $C_1$-$C_6$ alkyl; and $R^{12}$ at each occurrence is hydrogen or —OH. In some embodiments, $X^3$ is Boc and $X^1$ is Boc. Surprisingly, it has been found that when the compound of formula VIII-B or a salt thereof is exposed to acid in the presence of even small amounts of water, the deprotection may not go to completion and the deprotected product cannot be isolated as a solid powder. For example, 0.5 wt % or even 0.1 wt % water in a hydrohalic solution (e.g., HCl in an organic solvent) prevents ready isolation of the completely deprotected tetrapeptide of Formula VIII (i.e., $X^3$ is H and $X^1$ is H) in a non-sticky, powdered form. In contrast, deprotection under anhydrous conditions using, e.g., isopropyl alcohol and/or isopropyl acetate, gives the free tetrapeptide in good yield and high purity without chromatography or crystallization.

In some embodiments, the compound of formula VIII or a salt thereof is a compound of formula VIIIa or a salt thereof, and the compound of formula I or a salt thereof is a compound of formula Ia or a salt thereof:

VIIIa

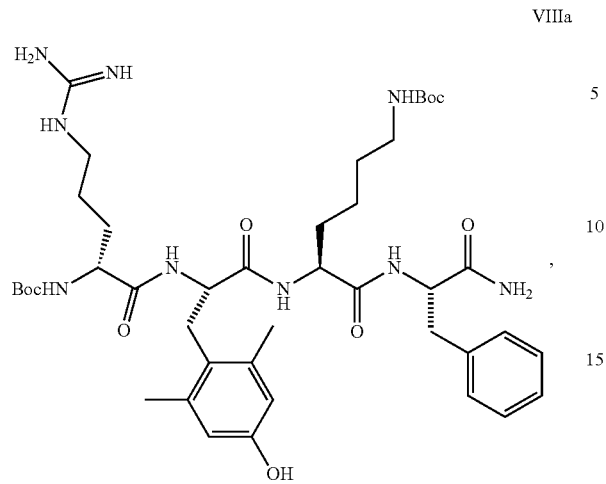

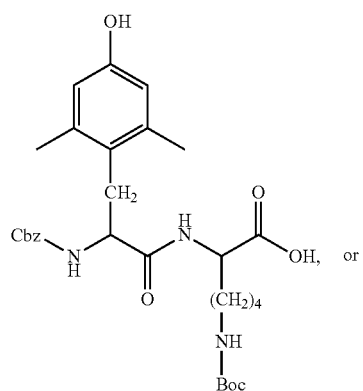
(I-Aa)

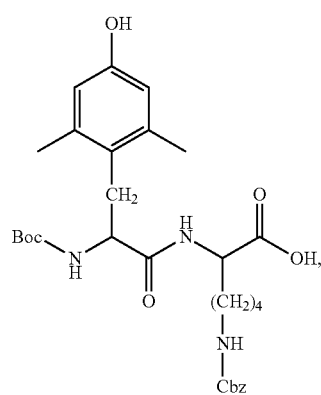
(I-Ab)

Ia

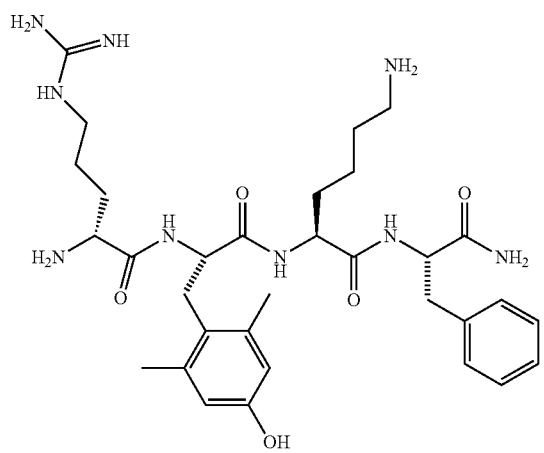

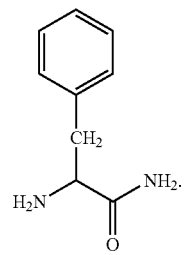
(I-Ba)

In some embodiments, the compound of formula I-C or a salt thereof is a compound of formula I-Ca, a stereoisomer thereof, or a salt of any of the foregoing, the compound of formula I-D or a salt thereof is a compound of formula I-Da, a stereoisomer thereof, or a salt of any of the foregoing:

In some embodiments, the compound of formula VIIIa or Ia is a salt as described herein. For example the compounds of formula VIIIa or Ia may be isolated as an aliphatic carboxylate (e.g., acetate, propionate, pivalate, $C_4$-$C_{18}$ fatty acids, etc.), hydrochloride, hydrobromide, alkyl sulfonate (e.g., mesylate, esylate, triflate), aryl sulfonates (e.g., tosylate), fumarate, succinate, tartrate, oxalate, phosphate, or sulfate salt.

In some embodiments, the compound of formula I-A or a salt thereof is a compound of formula I-Aa or I-Ab, or a stereoisomer thereof, or a salt of any of the foregoing, and the compound of formula I-B or a salt thereof is a compound of formula I-Ba, or a stereoisomer thereof, or a salt of any of the foregoing:

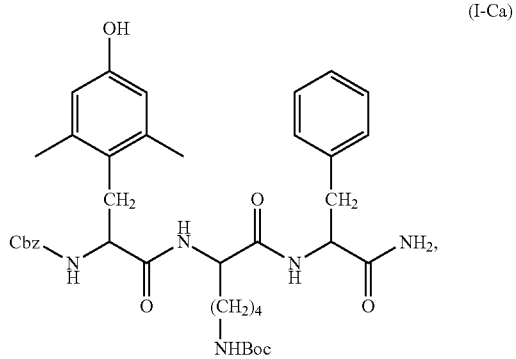
(I-Ca)

-continued

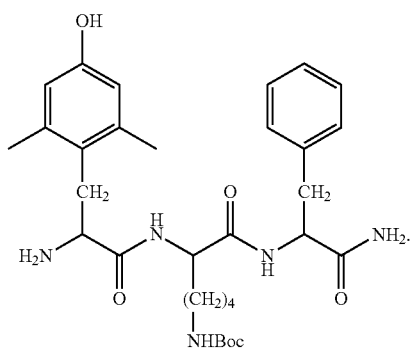
(I-Da)

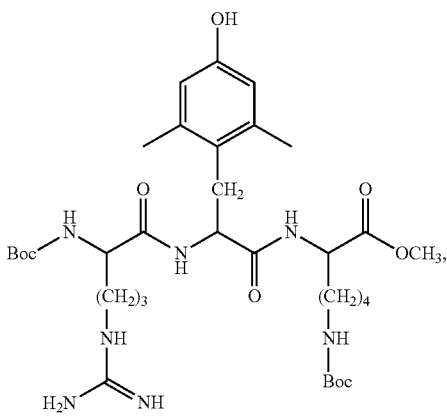
(II-Ca)

In some embodiments, the compound of formula I-E or a salt thereof is a compound of formula I-Ea or I-Eb, a stereoisomer thereof, or a salt of any of the foregoing, the compound of formula II-A or a salt thereof is a compound of formula II-Aa, a stereoisomer thereof, or a salt of any of the foregoing:

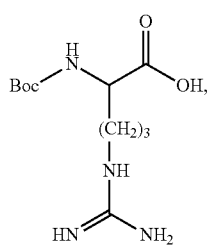
(I-Ea)

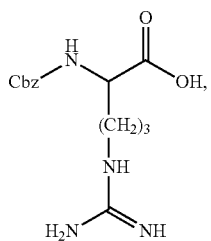
(I-Eb)

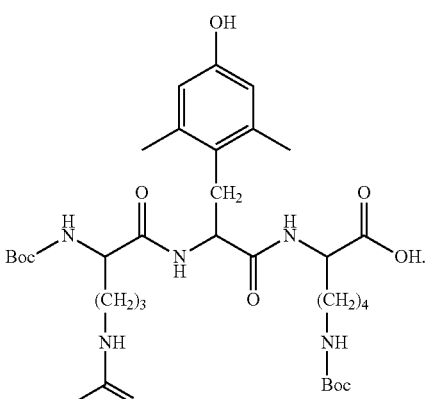
(II-Da)

In some embodiments, the compound of formula I-F or a salt thereof is a compound of formula I-Fa, a stereoisomer thereof, or a salt of any of the foregoing, the compound of formula I-G or a salt thereof is a compound of formula I-Ga, a stereoisomer thereof, or a salt of any of the foregoing, and the compound of formula I-H or a salt thereof is a compound of formula I-Ha, a stereoisomer thereof, or a salt of any of the foregoing:

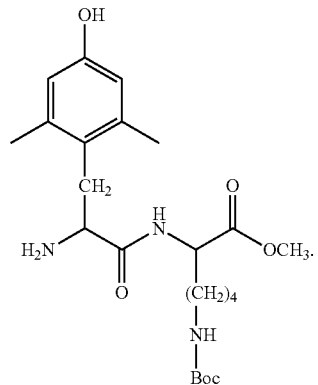
(II-Aa)

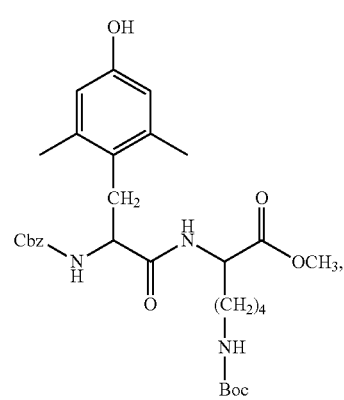
(I-Fa)

In some embodiments, the compound of formula II-C or a salt thereof is a compound of formula II-Ca, a stereoisomer thereof, or a salt of any of the foregoing, and the compound of formula II-D or a salt thereof is a compound of formula II-Da, a stereoisomer thereof or a salt of any of the foregoing:

-continued

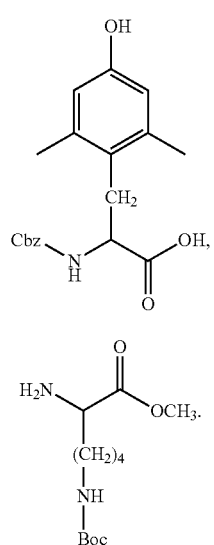
(I-Ga)

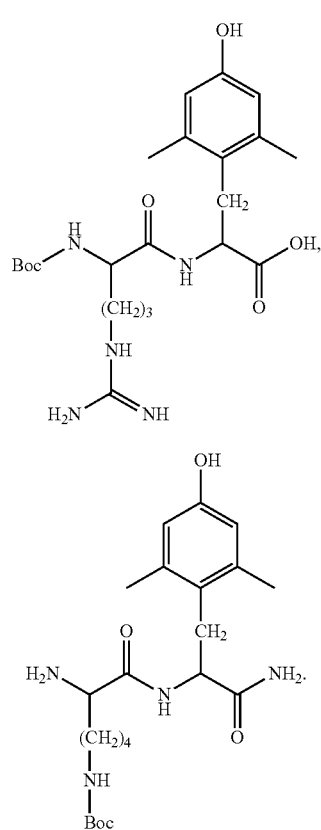
(I-Ha)

In some embodiments, the compound of formula III-A or a salt thereof is a compound of formula III-Aa, a stereoisomer thereof, or a salt of any of the foregoing, the compound of formula III-B or a salt thereof is a compound of formula III-Ba, a stereoisomer thereof, or a salt of any of the foregoing:

(III-Aa)

(III-Ba)

In some embodiments, the compound of formula III-C or a salt thereof is a compound of formula III-Ca, a stereoisomer thereof, or a salt of any of the foregoing, the compound of formula III-D or a salt thereof is a compound of formula III-Da, a stereoisomer thereof, or a salt of any of the foregoing:

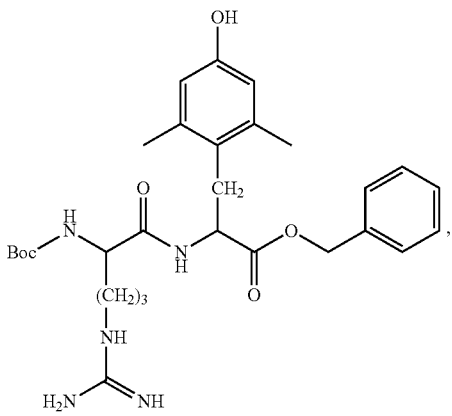
(III-Ca)

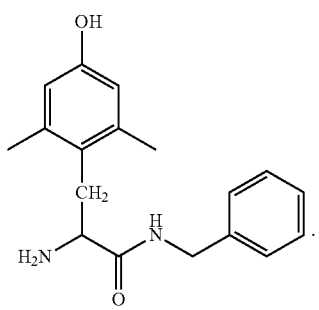
(III-Da)

In some embodiments, the compound of formula III-E is a compound of formula III-Ea, a stereoisomer thereof, or a salt of any of the foregoing, and the compound of formula III-F or a salt thereof, is a compound of formula III-Fa, a stereoisomer thereof, or a salt of any of the foregoing:

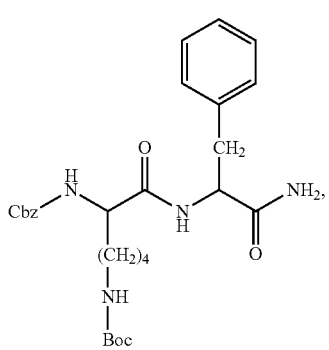
(III-Ea)

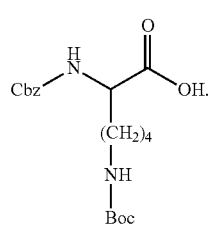
(III-Fa)

In some embodiments, the reacting of a compound of formula I-A or a salt thereof, wherein $A^1$ is OH with a compound of formula I-B or a salt thereof to form a compound of formula I-C or a salt thereof, the reacting of a compound of formula I-E or a salt thereof, wherein $A^2$ is OH with a compound of formula I-D or a salt thereof to form a compound of formula VIII or a salt thereof, the reacting of a compound of formula II-A or a salt thereof with a compound of formula I-E or a salt thereof, wherein $A^2$ is OH to form a compound of formula II-C or a salt thereof, the reacting of the compound of formula II-D or a salt thereof, wherein $A^4$ is OH with a compound of formula I-B or a salt thereof to form the compound of formula VIII or a salt thereof, the reacting of a compound of formula I-G or a salt thereof wherein $A^5$ is OH with a compound of formula I-H or a salt thereof to form the compound of formula I-F or a salt thereof, the reacting of a compound of formula III-A or a salt thereof wherein $A^6$ is OH with a compound of formula III-B or a salt thereof to form a compound of formula VIII or a salt thereof, the reacting of a compound of formula III-D or a salt thereof with a compound of formula I-E or a salt thereof wherein $A^2$ is OH to form a compound of formula III-C or a salt thereof, or the reacting of a compound of formula I-B or a salt thereof with a compound of formula III-F or a salt thereof wherein $A^7$ is OH to form a compound of formula III-E or a salt thereof is carried out under conditions comprising a coupling agent. In some embodiments, the coupling agent includes DCC, EDC, HATU, HBTU, HCTU, T3P, TBTU, TCTU, PyAOP, BOP, or PyBOP. In some embodiments, the coupling agent is EDC and the conditions optionally include HOBT. In some embodiments, the coupling agent may include BOP and the conditions optionally include HOBT. In some embodiments, the coupling agent may include HATU and the conditions optionally include HOAT. In some embodiments, the coupling agent is propylphosphonic anhydride ($T_3P$).

In any of the embodiments, the conditions of reacting a compound of formula I-A or a salt thereof with a compound of formula I-B or a salt thereof to form a compound of formula I-C or a salt thereof, the conditions of reacting a compound of formula I-D or a salt thereof with a compound of formula I-E or a salt thereof to form a compound of formula VIII or a salt thereof, the conditions of reacting a compound of formula II-A or a salt thereof with a compound of formula I-E or a salt thereof to form a compound of formula II-C or a salt thereof, the conditions of reacting the compound of formula II-D or a salt thereof with a compound of formula I-B or a salt thereof to form the compound of formula VIII or a salt thereof, the conditions of reacting a compound of formula I-G or a salt thereof with a compound of formula I-H or a salt thereof to form the compound of formula I-F or a salt thereof, the conditions of reacting a compound of formula III-A or a salt thereof with a compound of formula III-B or a salt thereof to form a compound of formula VIII or a salt thereof, the conditions of reacting a compound of formula III-D or a salt thereof with a compound of formula I-E or a salt thereof to form a compound of formula III-C or a salt thereof, the conditions of reacting a compound of formula I-B or a salt thereof with a compound of formula III-F or a salt thereof to form a compound of formula III-E or a salt thereof may further include a suitable solvent. Such solvents include, but are not limited to, alcohols (e.g., methanol ($CH_3OH$), ethanol (EtOH), isopropanol (iPrOH), trifluorethanol (TFE), butanol (BuOH)), halogenated solvents (e.g., methylene chloride ($CH_2Cl_2$), chloroform ($CHCl_3$), benzotrifluoride (BTF; $PhCF_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile ($CH_3CN$), proprionitrile ($CH_3CH_2CN$), benzonitrile (PhCN)), sulfoxides (e.g., dimethyl sulfoxide), sulfones (e.g., sulfolane), water, or mixtures of any two or more thereof. In any of the above embodiments, it may be that the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof. In some embodiments, the solvent is dimethylformamide (DMF) or $CH_2Cl_2$. In any of the above embodiments, the conditions may further include a base. The base may be an inorganic base, such as $Na_2CO_3$ or $NaHCO_3$, or an organic base such as 1,8-diazabicyclo[5.4.0]undec-7-ene (DBU), pyridine, N,N-dimethyl-4-aminopyridine (DMAP) or a trialkyl amine. Suitable trialkyl amines include, but are not limited to, trimethyl amine, triethyl amine, dimethylethyl amine, and diisopropylethyl amine. When the base includes an inorganic base, the suitable solvent may further include water.

In any of the above embodiments, it may be that the conditions may comprise a temperature from about –40° C. to about 150° C., for example at about –40° C., about –35° C., about –30° C., about –25° C., about –20° C., about –15° C., about –10° C., about –5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., and any range including and between any two of these values.

In some embodiments, $Y^1$ is an amino protecting group susceptible to acid-mediated removal. In some embodiments, $Y^1$ is tert-butyloxycarbonyl (Boc). In some embodiments, converting the compound of formula I-C or a salt thereof to a compound of formula I-D or a salt thereof comprising combining the compound of formula I-C or a salt thereof with a cleaving acid to produce the compound of formula I-D or a salt thereof. In some embodiments, the process further includes isolating the compound of formula I-D or a salt thereof. In some embodiments, converting the compound of formula I-F or a salt thereof to a compound of formula II-A or a salt thereof comprising combining the compound of formula I-F or a salt thereof with a cleaving acid to produce the compound of formula II-A or a salt thereof. In some embodiments, the process further includes isolating the compound of formula II-A or a salt thereof.

In some embodiments, $Y^2$ is an amino protecting group susceptible to acid-mediated removal. In some embodiments, $Y^2$ is tert-butyloxycarbonyl (Boc). In some embodiments, converting the compound of formula III-E or a salt thereof to a compound of formula III-B or a salt thereof comprising combining the compound of formula III-E or a salt thereof with a cleaving acid to produce the compound of formula III-B or a salt thereof. In some embodiments, the process further includes isolating the compound of formula III-B or a salt thereof.

Cleaving acids include halogen acids, carboxylic acids, phosphonic acids, phosphoric acids, sulfinic acids, sulfonic acids, sulfuric acids, sulfamic acids, boric acids, boronic acids, an acid resin, or combinations of any two or more thereof. Representative examples include, but are not limited to, hydrofluoric acid, hydrochloric acid (HCl), hydrobromic acid, hydroiodic acid, acetic acid (AcOH), fluoroacetic acid, trifluoroacetic acid (TFA), chloroacetic acid, benzoic acid, phosphoric acid, methanesulfonic acid, benzenesulfonic acid, p-toluene sulfonic acid, trifluoromethanesulfonic acid, and sulfuric acid. In some embodiments, the process includes any two or more of the aforementioned cleaving acids. The combining with the cleaving acid may occur at temperatures from about −40° C. to about 150° C. Such an embodiment may be performed at about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., and any range including and between any two of these values. In any of the above embodiments, it may be that after combining with the cleaving acid the temperature is raised to a temperature of about 10° C., 15° C., 20° C., 25° C., 30° C., 35° C., 40° C., 45° C., 50° C., or any range including and between any two of these values.

In some embodiments, the combining with the cleaving acid includes a protic solvent, a polar aprotic solvent, or a mixture of the two. Protic solvents as used herein include, but are not limited to, alcohols (e.g., methanol ($CH_3OH$), ethanol (EtOH), isopropanol (iPrOH), trifluorethanol (TFE), butanol (BuOH)), carboxylic acids (e.g., formic acid, acetic acid, propanoic acid, butanoic acid, pentanoic acid, lauric acid, stearic acid, deoxycholic acid, glutamic acid, glucuronic acid), water, or mixtures of any two or more thereof. Polar aprotic solvents as used herein include halogenated solvents (e.g., methylene chloride ($CH_2Cl_2$), chloroform ($CHCl_3$), benzotrifluoride (BTF; $PhCF_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile ($CH_3CN$), proprionitrile ($CH_3CH_2CN$), benzonitrile (PhCN)), sulfoxides (e.g., dimethyl sulfoxide), sulfones (e.g., sulfolane), or mixtures of any two or more thereof. In any of the above embodiments, it may be that combining with the cleaving acid further includes methanol ($CH_3OH$), ethanol (EtOH), isopropanol (iPrOH), trifluorethanol (TFE), butanol (BuOH), methylene chloride ($CH_2Cl_2$), chloroform ($CHCl_3$), benzotrifluoride (BTF; $PhCF_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile ($CH_3CN$), proprionitrile ($CH_3CH_2CN$), benzonitrile (PhCN), dimethyl sulfoxide, sulfolane, water, or mixtures of any two or more thereof.

In some embodiments, $Y^1$ is an amino protecting group resistant to acid-mediated removal and susceptible to hydrogen-mediated removal. In some embodiments, $Y^1$ is Cbz. In some embodiments, converting the compound of formula I-C or a salt thereof to a compound of formula I-D or a salt thereof comprising combining the compound of formula I-C or a salt thereof with a hydrogen source to produce the compound of formula I-D or a salt thereof. In some embodiments, the process further includes isolating the compound of formula I-D or a salt thereof. In some embodiments, converting the compound of formula I-F or a salt thereof to a compound of formula II-A or a salt thereof comprising combining the compound of formula I-F or a salt thereof with a hydrogen source to produce the compound of formula II-A or a salt thereof. In some embodiments, the process further includes isolating the compound of formula II-A or a salt thereof.

In some embodiments, $Y^2$ is an amino protecting group resistant to acid-mediated removal and susceptible to hydrogen-mediated removal. In some embodiments, $Y^2$ is Cbz. In some embodiments, converting the compound of formula III-E or a salt thereof to a compound of formula III-B comprising combining the compound of formula III-E or a salt thereof with a hydrogen source to produce the compound of formula III-B or a salt thereof. In some embodiments, the process further includes isolating the compound of formula III-B or a salt thereof.

The term "hydrogen source" means a source for providing two hydrogen atoms. In any of the embodiments and aspects described herein, it may be that the hydrogen source includes molecular hydrogen, formic acid, formate salts, diimide, cyclohexene, or cyclohexadiene or combinations of any two or more thereof. Formate salts include, but are not limited to, $NH_4OC(O)H$ and may also be represented by $(M)_x(OCHO)_y$, where M is a alkali metal or an alkaline earth metal, x is 1, 2, or 3 and where y is 1, 2, or 3. In some embodiments, the hydrogen source is hydrogen gas. In any of the embodiments and aspects described herein, combining the compound with a hydrogen source further comprises a transition metal catalyst, which includes, but is not limited to, cobalt (Co), iridium (Ir), molybdenum (Mo), nickel (Ni), platinum (Pt), palladium (Pd), rhodium (Rh), ruthenium (Ru), tungsten (W), or combinations of any two or more thereof. In some embodiments, the transition metal catalyst includes Pd. In any of the embodiments and aspects described herein, the transition metal catalyst includes a support material. Support materials include, but are not limited to, carbon, carbonate salts, silica, silicon, silicates, alumina, clay, or mixtures of any two or more thereof. For example, in some embodiments, the transition metal catalyst is Pd on carbon (Pd/C). In some embodiments, the transition metal catalyst is Pd on silicon (Pd/Si). In embodiments of the transition metal catalyst that include a support material, the amount of transition metal in the combined transition metal/support material mass may be from about 0.01 wt % to about 80 wt %. The amount of transition metal may be about 0.01 wt %, 0.05 wt %, 0.1 wt %, about 0.5 wt %, about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, or any range including and in between any two of these values. In some embodiments, the transition metal catalyst is Pd on carbon, and the amount of transition metal is 5 wt %, i.e., 5% Pd/C. In some embodiments, the transition metal catalyst is Pd on carbon, and the amount of transition metal is 10 wt %, i.e., 10% Pd/C. In some embodiments, the transition metal catalyst is Pd on silicon, and the amount of transition metal is 5 wt %, i.e., 5% Pd/Si. In some embodiments, the transition metal catalyst is Pd on silicon, and the amount of transition metal is 10 wt %, i.e., 10% Pd/Si. In any of the embodiments and aspects described herein, it may be that a solvent is included in addition to the hydrogen source and transition metal catalyst. Representative solvents include, but are not limited to, alcohols, halogenated solvents, ethers, esters, ketones, amides, nitriles, sulfoxides, sulfones, water, or mixtures of any two or more thereof. In any of the above embodiments, it may be that the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof. In any of the embodiments and aspects described herein, the solvent may further include an acid. The acid may be present in a suitable amount, including a catalytic amount. Such acids include, but are not limited to, a mineral acid (e.g., HCl, HBr, HF, $H_2SO_4$, $H_3PO_4$, $HClO_4$), a carboxylic acid (e.g., formic acid, acetic acid, propanoic acid, butanoic acid, pentanoic acid, lauric acid, stearic acid, deoxycholic acid, glutamic acid, glucuronic acid), boronic acid, a sulfinic acid, a sulfamic acid, or mixtures of any two or more thereof. In any of the above embodiments, it may be that the solvent further includes, HCl, HBr, HF, $H_2SO_4$, $H_3PO_4$, $HClO_4$, formic acid, acetic acid, propanoic acid, butanoic acid, pentanoic acid, lauric acid, stearic acid, deoxycholic acid, glutamic acid, glucuronic acid, boronic acid, a sulfinic acid, a sulfamic acid, or mixtures of any two or more thereof. It is to be noted that when formic acid is included as the acid, formic acid may also be a hydrogen source.

In some embodiments, $Y^1$ is an amino protecting group resistant to acid-mediated removal and susceptible to base-mediated removal. In some embodiments, $Y^1$ is Fmoc. In some embodiments, converting the compound of formula I-C or a salt thereof to a compound of formula I-D or a salt thereof comprising combining the compound of formula I-C or a salt thereof with a base to produce the compound of formula I-D or a salt thereof. In some embodiments, the process further includes isolating the compound of formula I-D or a salt thereof. In some embodiments, converting the compound of formula I-F or a salt thereof to a compound of formula II-A or a salt thereof comprising combining the compound of formula I-F or a salt thereof with a hydrogen source to produce the compound of formula II-A or a salt thereof. In some embodiments, the process further includes isolating the compound of formula II-A or a salt thereof.

In some embodiments, $Y^2$ is an amino protecting group resistant to acid-mediated removal and susceptible to base-mediated removal. In some embodiments, $Y^2$ is Fmoc. In some embodiments, converting the compound of formula III-E or a salt thereof to a compound of formula III-B or a salt thereof comprising combining the compound of formula III-E or a salt thereof with a base to produce the compound of formula III-B or a salt thereof. In some embodiments, the process further includes isolating the compound of formula III-B or a salt thereof.

In some embodiments the base that mediates removal of the amino protecting group susceptible to base-mediated removal is N-methylpyrrolidine, 1,4-bis-(3-aminopropyl)piperazine, DBU, hydrazine, DIEA, dimethylaminopyridine, NaOH, KOH, LiOH, $Na_2CO_3$, $NaHCO_3$, $K_2CO_3$, $KHCO_3$, $Li_2CO_3$, $LiHCO_3$, a primary or secondary amine, such as ammonia, ethanolamine, diethylamine, cyclohexylamine, pyrrolidine, piperidine, morpholine, piperazine, dixyxlohexylamine, etc. In any of the embodiments and aspects described herein, it may be that a solvent is included in addition to the base. Representative solvents include, but are not limited to, alcohols, halogenated solvents, ethers, esters, ketones, amides, nitriles, sulfoxides, sulfones, water, or mixtures of any two or more thereof. In any of the above embodiments, it may be that the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof.

In some embodiments, the process further includes isolating the compound of formula VIII or a salt thereof. In any of the above embodiments, it may be that the conditions to isolating the compound of formula VIII or a salt thereof further include a suitable solvent. Such solvents include, but are not limited to, alcohols (e.g., methanol ($CH_3OH$), ethanol (EtOH), isopropanol (iPrOH), trifluorethanol (TFE), butanol (BuOH)), halogenated solvents (e.g., methylene chloride ($CH_2Cl_2$), chloroform ($CHCl_3$), benzotrifluoride (BTF; $PhCF_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile ($CH_3CN$), proprionitrile ($CH_3CH_2CN$), benzonitrile (PhCN)), sulfoxides (e.g., dimethyl sulfoxide), sulfones (e.g., sulfolane), water, or mixtures of any two or more thereof. In any of the above embodiments, it may be that the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof. In some embodiments, the suitable solvent includes dimethylformamide (DMF). In some embodiments, the suitable solvent includes dimethylacetamide (DMA). In some embodiments, the suitable solvent includes $CH_2Cl_2$.

In some embodiments of any aspects described herein, if $X^3$ is $R^2$, then $R^1$ is not hydrogen. In some embodiments, if $X^3$ is $R^2$, then neither $R^1$ nor $R^2$ is hydrogen. In some embodiments, when $Z^5$ and/or $Z^6$ is —NHC(NH)—NH—$X^2$, X" is hydrogen. In some embodiments, when $Z^5$ and/or $Z^6$ is —NHC(N—$X^4$)—NH—$X^2$, $X^1$ is hydrogen and at least one of $X^2$ and $X^4$ is not H. In some embodiments, when $X^2$ is an amino protecting group resistant to acid-mediated removal and susceptible to hydrogen-mediated removal, $X^1$ is hydrogen. In some embodiments, when $X^1$ is an amino protecting group resistant to acid-mediated removal and susceptible to hydrogen-mediated removal, $X^2$ is hydrogen.

In any of the above embodiments, it may be that $Y^1$ is Boc, Trt, Bpoc, Ddz or Nps; $X^1$ at each occurrence is independently hydrogen, Alloc, Cbz, or 2-ClCbzl; $X^2$ at each occurrence is independently hydrogen, Alloc, Cbz, or 2-ClCbz; and $X^4$ at each occurrence is independently hydrogen, nitro, Alloc, Cbz, or 2-ClCbz.

In another aspect, provided is a process for preparing a peptide of formula I or a salt thereof:

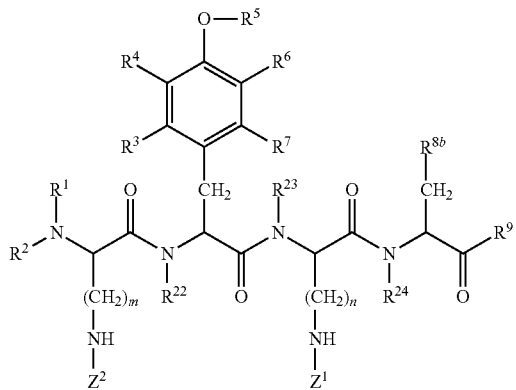

(I)

or a pharmaceutically acceptable salt thereof, wherein $R^1$ and $R^2$ are each independently selected from (i) hydrogen;

(ii) substituted or unsubstituted $C_1$-$C_6$ alkyl;

(iii) substituted or unsubstituted aralkyl;

(iv) substituted or unsubstituted $C_3$-$C_8$ cycloalkyl or cycloalkylalkyl;

(v) substituted or unsubstituted $C_2$-$C_6$ alkenyl;

(vi) an amino protecting group;

or $R^1$ and $R^2$ together form a 3, 4, 5, 6, 7, or 8 membered substituted or unsubstituted heterocyclyl or heteroaryl group;

$R^3$, $R^4$, $R^6$, and $R^7$ are each independently selected from hydrogen, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^5$ is selected from hydrogen, or a $C_1$-$C_6$ alkyl or perhaloalkyl, aralkyl, —C(O)-alkyl, —C(O)-aryl, or —C(O)-aralkyl group, wherein each alkyl, aryl or aralkyl group is substituted or unsubstituted;

$R^{8b}$ is

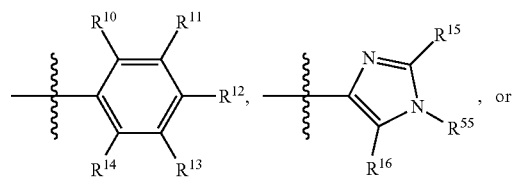

-continued

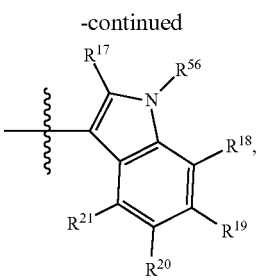

where $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted; $R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^9$ is OR' or NR'R'';

R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

R'' is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{22}$, $R^{23}$, and $R^{24}$ are each independently hydrogen or a $C_1$-$C_4$ alkyl;

$Z^1$ and $Z^2$ are each independently hydrogen, —C(NH)—NH$_2$, or a substituted or unsubstituted alkyl, aryl, or aralkyl group;

n is 1, 2, 3, 4, or 5; and m is 1, 2, 3, 4, or 5, the process comprises converting the compound of formula VIII or a salt thereof described herein wherein at least one of $X^1$, $X^2$, $X^3$ and $X^4$ in the compound of formula VIII or a salt thereof is an amino protecting group to the compound of formula I or a salt thereof.

In some embodiments, $R^1$, $R^2$, $R^4$, $R^5$, and $R^6$ are each hydrogen; $R^3$ and $R^7$ are each methyl; $R^8$ is

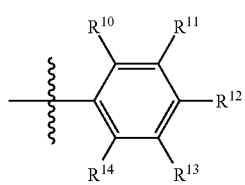

where $R^{10}$, $R^{11}$, $R^{12}$, $R^{13}$, and $R^{14}$ are all hydrogen; $R^9$ is NH$_2$; $Z^1$ is hydrogen, $Z^2$ is —C(NH)—NH$_2$; n is 4; and m is 3.

In any of the above embodiments, it may be that $R^4$, $R^5$, and $R^6$ are each hydrogen; $R^3$ and $R^7$ are methyl; $R^8$ is

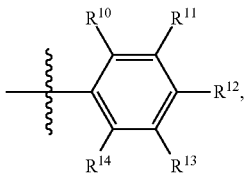

where $R^{10}$, $R^{11}$, $R^{12}$, $R^{13}$, and $R^{14}$ are all hydrogen; $Z^1$ and $Z^5$ are hydrogen; $Z^2$ is —C(NH)—NH$_2$; $Z^6$ is —C(N—X$^4$)—NH—X$^2$ wherein at least one of $X^2$ and $X^4$ is not H; n is 4; and m is 3.

In any of the above embodiments, it may be that $R^4$, $R^5$, and $R^6$ are each hydrogen; $R^3$ and $R^7$ are methyl; $R^8$ is

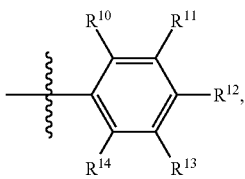

where $R^{10}$, $R^{11}$, $R^{12}$, $R^{13}$, and $R^{14}$ are all hydrogen; $X^2$ is not H; $X^4$ is not H; $Z^1$ and $Z^5$ are hydrogen; $Z^2$ is —C(NH)—NH$_2$; $Z^6$ is —C(N—X$^4$)—NH—X$^2$; n is 4; and m is 3.

In some embodiments, the peptide prepared by the process includes residues at the 1$^{st}$ and 3$^{rd}$ positions selected from Arg, D-Arg, His, D-His, Lys, D-Lys, Orn (ornithine), D-OrnAah (2-amino-6-amidinohexanoic acid), and D-Aah. In certain embodiments, the residues at the 2$^{nd}$ and 4$^{th}$ positions are selected from Phe, Tyr, His, Trp, and 2'6'-Dmt. All residues are of the L configuration unless indicated to be the D-configuration. In some embodiments, the peptides prepared by the process include one or more of the peptides of Table A* or a steroisomer and/or salt thereof.

TABLE A

D-Arg-2'6'-Dmt-Lys-Phe-NH$_2$
D-Arg-2'6'-Dmt-Lys-Trp-NH$_2$
D-Arg-2'6'-Dmt-Lys-Tyr-NH$_2$
D-Arg-2'6'-Dmt-Lys-2'6'-Dmt-NH$_2$
D-Arg-Tyr-Lys-Phe-NH$_2$
D-Arg-Phe-Lys-Phe-NH$_2$
D-Arg-Phe-Lys-2'6'-Dmt-NH$_2$
D-Arg-Trp-Lys-Phe-NH$_2$
D-Arg-Trp-Lys-Trp-NH$_2$
D-Arg-Trp-Lys-2'6'-Dmt-NH$_2$
D-Lys-2'6'-Dmt-Lys-Phe-NH$_2$
Arg-2'6'-Dmt-Lys-Phe-NH$_2$
D-Aah-2'6'-Dmt-Lys-Phe-NH$_2$

In some embodiments, the peptide includes the amino acid sequence D-Arg-2'6'-Dmt-Lys-Phe-NH$_2$.

In some embodiments, at least one of $X^1$, $X^2$, $X^3$ and $X^4$ in the compound of formula VIII or a salt thereof is an amino protecting group resistant to acid-mediated removal and susceptible to hydrogen-mediated removal, the process comprises reacting the compound of formula VIII or a salt thereof with a hydrogen source and a transition metal catalyst to form a compound of formula I.

In any of the above embodiments, the hydrogen source and the transition metal catalyst are as described herein. In any of the above embodiments, it may be that the combination of the compound of formula VIII or a salt thereof, the hydrogen source, and the transition metal catalyst is subjected to a temperature from about −20° C. to about 150° C. Such an embodiment may be performed at about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., and any range including and between any two of these values.

In some embodiments, at least one of $X^1$, $X^2$, $X^3$ and $X^4$ in the compound of formula VIII or a salt thereof is an amino protecting group susceptible to acid-mediated removal, the process comprises reacting the compound of formula VIII or a salt thereof with a cleaving acid described herein to form a compound of formula I or a salt thereof.

In some embodiments, the process further includes isolating the compound of formula I or a salt thereof. In some embodiments, the process includes preparing a pharmaceutically acceptable salt of the compound of formula I or a salt thereof. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, alkylammonium, calcium, cupric, cuprous, nickel, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, diisopropylethylamine, ethanolamine, ethylenediamine, N-ethylmorpholine, N-ethylpiperidine, glucamine, glucosamine, histidine, hydrabamine, imidazole, isopropylamine, lysine, methylglucamine, morpholine, N-methylmorpholine, piperazine, piperidine, pyridine, lutidine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, phosphorous, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), fatty acids (lauric, myristic, oleic, stearic, palmitic), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the pharmaceutically acceptable acids include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid. In some embodiments, the salt is an acetate salt. Additionally or alternatively, in other embodiments, the salt is a trifluoroacetate salt. In some embodiments, the salt is a hydrochloride, tosylate or tartrate salt. In other embodiments, the salt is an anhydrous hydrochloride salt.

In another aspect, an isomer of the compound of formula I-G, (L)-I-G, and III-D, (L)-III-D or a salt of any of the foregoing can be prepared from a compound of formula XV or a salt thereof:

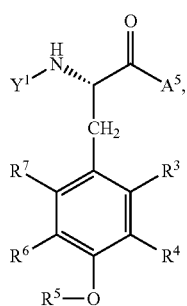

((L)-I-G)

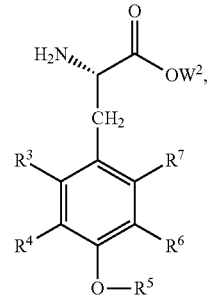

((L)-III-D)

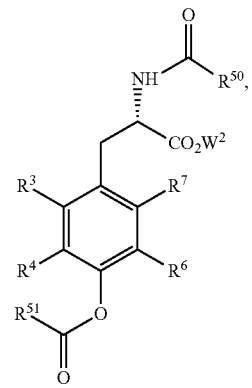

(XV)

wherein $R^{50}$ and $R^{51}$ are each independently hydrogen or a substituted or unsubstituted $C_1$-$C_6$ alkyl, aryl, or cycloalkyl group, and $W^2$, $R^3$, $R^4$, $R^5$, $R^6$ and $R^7$ are as defined herein. In some embodiments, $R^4$ and $R^6$ are each hydrogen. In some embodiments, $R^3$, $R^7$, $R^{50}$ and $R^{51}$ are each methyl.

In one aspect, the compound of formula (L)-I-G or a salt thereof is prepared from a compound of formula XV or a salt thereof by a method comprising converting the —NHCOR$^{50}$ group of the compound of formula XV or a salt thereof to —NH$_2$ by for example, reacting the compound of formula XV or a salt thereof with an aqueous HCl solution or an aqueous ammonia solution, followed by reacting the —NH$_2$ of the resulting compound with a compound $Y^1$-Lv or a salt thereof, an organic base, and an appropriate solvent, wherein Lv is a leaving group such as halo, —O—$Y^1$, or —O—C(O)Cl. In some embodiments, $Y^1$ is Boc and $Y^1$-Lv is Boc$_2$O. In some embodiments, $Y^1$ is Cbz and $Y^1$-Lv is benzyl chloroformate (CbzCl). In some embodiments, the base is triethylamine (Et$_3$N), 1,8-diazabicyclo[5.4.0]undec-7-ene (DBU), diisopropylethylamine (DIPEA), pyridine or 4-dimethylaminopyridine (DMAP), or a combination of any two or more thereof. In some embodiments, the base is DMAP. The solvent may include an alcohol, a halogenated solvent, an ether, an ester, a ketone, an amide, a nitrile, a sulfoxide, a sulfone, water, or mixtures of any two or more thereof. In any of the above embodiments, it may be that the solvent includes CH$_3$OH, EtOH, iPrOH, TFE, BuOH, CH$_2$Cl$_2$, CHCl$_3$, PhCF$_3$, THF, 2Me-THF, DME, dioxane, ethyl acetate, isopropyl acetate, acetone, methylethyl ketone, methyl isobutyl ketone, DMF, DMA, CH$_3$CN, CH$_3$CH$_2$CN, PhCN, dimethylsulfoxide, sulfolane, water, or mixtures of any two or more thereof. In some embodiments, the solvent is methylene chloride (CH$_2$Cl$_2$), chloroform (CHCl$_3$), tetrahydrofuran (THF), 2-methyltetrahydrofuran, dimethoxyethane (DME), dioxane or a mixture of any two or more thereof. In some embodiments, the solvent is methylene chloride. In some embodiments, the method of converting the compound of formula XV or a salt thereof to the compound of formula (L)-I-G or a salt thereof further comprises converting the groups COOW$^2$ of the compound of formula XV or a salt thereof to COOH and/or converting the group OCOR$^{51}$ of the compound of formula XV or a salt thereof to OH. Such conversions are generally known in the art. In some embodiments, the converting is under conditions that include an aqueous solution of an alkali metal hydroxide (e.g., LiOH, NaOH or KOH) or an alkaline earth metal hydroxide (e.g., Ca(OH)$_2$ or Mg(OH)$_2$). In some embodiments, the converting is under conditions that include an aqueous solution of NaOH. In some embodiments, W$^2$ is benzyl and converting COOW$^2$ to COOH is under conditions comprising a hydrogen source and a transition metal catalyst as described herein. In some embodiments, the method further includes converting the resulting OH group to OR$^5$ by reacting the OH group with a compound of R$^5$-Lv$^2$ wherein R$^5$ is as defined herein but not a hydrogen, and Lv$^2$ is a leaving group such as Cl or Br to form the compound of formula (L)-I-G or a salt thereof wherein A$^5$ is OH. In some embodiments, the method further comprises converting the compound of formula (L)-I-G or a salt thereof wherein A$^5$ is OH to an anhydride, such as a compound of formula (L)-I-G or a salt thereof wherein A$^5$ is —OC(O)—R$^{59}$ by a method comprising reacting the compound of formula (L)-I-G or a salt thereof wherein A$^5$ is OH with ClC(O)—R$^{59}$ to form the compound of formula (L)-I-G or a salt thereof wherein A$^5$ is —OC(O)—R$^{59}$. In some aspects, the compound of (L)-I-G or a salt thereof wherein A$^5$ is OH is further converted to an active ester, such as a compound of formula (L)-I-G or a salt thereof wherein A$^5$ is —O—R$^{58}$ by a method comprising reacting the compound of formula (L)-I-G or a salt thereof wherein A$^5$ is OH with Lv$^1$-R$^{58}$ or a salt thereof as described herein. In some aspects, the compound of (L)-I-G or a salt thereof wherein A$^5$ is OH is further converted to a compound of (L)-I-G or a salt thereof wherein A$^5$ is F by a method comprising reacting the compound of (L)-I-G or a salt thereof wherein A$^5$ is OH with a fluorinating agent described herein. In some aspects, the compound of formula (L)-I-G wherein A$^5$ is OH is further converted to a compound of formula (L)-I-G wherein A$^5$ is Cl by a method comprising reacting the compound of formula (L)-I-G or a salt thereof wherein A$^5$ is OH with a chlorinating agent described herein. In some aspects, the compound of formula (L)-I-G or a salt thereof wherein A$^5$ is OH is further converted to a compound of formula (L)-I-G or a salt thereof wherein A$^5$ is Br by a method comprising reacting the compound of formula (L)-I-G or a salt thereof wherein A$^5$ is OH with brominating agent described herein. In some embodiments, the process further includes isolating the compound of formula (L)-I-G or a salt thereof.

In one aspect, the compound of formula (L)-III-D or a salt thereof is prepared from a compound of formula XV or a salt thereof by a method comprising converting —NHCOR$^{50}$ group of the compound of formula XV or a salt thereof to —NH$_2$ by for example, reacting the compound of formula XV or a salt thereof with an aqueous HCl solution or an aqueous ammonia solution. In some embodiments, the method of converting the compound of formula XV or a salt thereof to the compound of formula (L)-III-D or a salt thereof further comprises ester hydrolysis conditions under which the group OCOR$^{51}$ of the compound of formula XV or a salt thereof is hydrolyzed to OH to form the compound of formula (L)-III-D wherein R$^5$ is hydrogen. Such conditions are generally known in the art. In some embodiments, the compound of formula (L)-III-D or a salt thereof wherein R$^5$ is hydrogen is further converted to a compound of formula (L)-III-D or a salt thereof wherein R$^5$ is other than hydrogen by reacting the compound of formula (L)-III-D or a salt thereof wherein R$^5$ is hydrogen with a compound of R$^5$-Lv$^2$ or a salt thereof wherein R$^5$ is as defined herein but not a hydrogen, and Lv$^2$ is a leaving group such as Cl or Br to form the compound of formula (L)-III-D or a salt thereof. In some embodiments, the process further includes isolating the compound of formula (L)-III-D or a salt thereof.

In some embodiments, the yield of converting the compound of formula XV or a salt thereof to the compound of formula (L)-I-G or (L)-III-D or a salt thereof is at least about 50%, or at least about 60%, or at least about 70%, or at least about 80%, or at least about 90%, or at least about 95%. In some embodiments, the compound of formula (L)-I-G or (L)-III-D or a salt thereof is isolated in a purity of at least about 90%, or at least about 95%, or at least about 97%, or least about 99% in a yield of at least about 50%, or at least about 60% or at least about 70%, or at least about 80%, or at least about 90%, or at least about 95%.

In some embodiments, the compound of formula XV or a salt thereof is prepared by a method described in, e.g., PCT/US2014/072264, filed Dec. 23, 2014, titled Pharmaceutically Relevant Aromatic-Cationic Peptides and Methods of Generating the Same.

It is surprising that such a compound can be incorporated in a peptide without protecting the hydroxyl group on the phenol.

In another aspect, provided is an intermediate useful in the processes of this technology as described herein, such as a compound of formula I-A, I-B, I-C, I-D, I-E, I-F, I-G, I-H, II-A, II-C, II-D, III-A, III-B, III-E, or III-F, or a salt of any of the foregoing, and methods of preparing the intermediates as described herein.

EXAMPLES

The present technology is further illustrated by the following examples, which should not be construed as limiting in any way. For each of the examples below, any peptide described herein could be used. By way of example, but not by limitation, the peptide used in the example below could be or D-Arg-2'6'-Dmt-Lys-Phe-NH$_2$. In one embodiment, the peptide is a pharmaceutical salt for example, but not limited to, e.g., a tartrate salt, acetate salt, or trifluoroacetate salt.

Terms and Abbreviations:
    ACN=acetonitrile,
    Atm=atmosphere,
    BOC=Boc=tert-butoxycarbonyl,
    BOP reagent=Benzotriazol-1-yloxytris(dimethylamino) phosphonium hexafluorophosphate,
    Bn=benzyl,
    br=broad,
    t-BuOH=tert-butyl alcohol,
    Cat.=catalytic,
    Conc.=conc=concentrated,
    d=doublet,
    dd=doublet of doublets,
    ddd=doublet of doublet of doublets,
    dt=doublet of triplets,
    DCM=dichloromethane (CH$_2$Cl$_2$),
    Dess-Martin periodinane=1,1,1-Tris(acetyloxy)-1,1-dihydro-1,2-benziodoxol-3-(1H)-one
    DIAD=diisopropyl azodicarboxylate,
    DIPEA=N,N-diisopropylethylamine,
    DMF=N,N-dimethylforamide, DMSO=dimethyl sulfoxide,
EDC=N-ethyl-N'-(3-dimethylaminopropyl)carbodiimide hydrochloride
Et$_2$O=diethyl ether,
Et$_3$N=triethylamine,
EtOAc=ethyl acetate,
EtOH=ethyl alcohol,
eq. or equiv.=equivalent(s),
h=hour(s),
HATU=N,N,N',N'-tetramethyl-O-(7-azabenzotriazol-1-yl)uronium hexafluorophosphate
H$_2$O=water,
HCl=hydrochloric acid
HPLC=high performance liquid chromatography,
HOAc=acetic acid,
HOBt=1-hydroxybenzotriazole
IPA=isopropyl alcohol,
ISCO=normal phase silica gel cartridges supplied by Teledyne ISCO,
K$_2$CO$_3$=potassium carbonate,
LiBH$_4$=lithium tetrahydroborate,
LiBr=lithium bromide,
LiCl=lithium chloride,
LAH=lithium tetrahydroaluminate,
m=multiplet,
min.=min=minute(s)
MgCl$_2$=magnesium chloride
MeOH=methanol,
2-MeTHF=2-methyltetrahydrofuran,
MsCl=methanesulfonyl chloride,
MTBE=methyl tert-butyl ether,
NaHCO$_3$=sodium bicarbonate,
Na$_2$SO$_4$=sodium sulfate,
NH$_4$OH=ammonium hydroxide,
NH$_4$OAc=ammonium acetate,
NH$_4$Cl=ammonium chloride,
NMR=nuclear magnetic resonance,
NMP=N-methylpyrrolidinone,
Pd-C=palladium on activated carbon
p=pentet,
PMB=p-methoxybenzyl,
PMBCl=p-methoxybenzyl chloride,
ret=retention
rt=room temperature,
s=singlet,
sat=saturated,
t=triplet,
TFA=trifluoroacetic acid,
TBDPS=t-butyldiphenylsilyl,
TBS=t-butyldimethylsilyl,
THF=tetrahydrofuran,
TLC=thin layer chromatography
No protecting group is needed on the phenol OH for the coupling reactions.

Example 1. Preparation of Cbz-DMT (1)

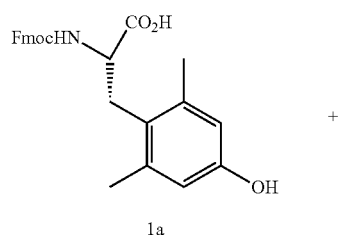

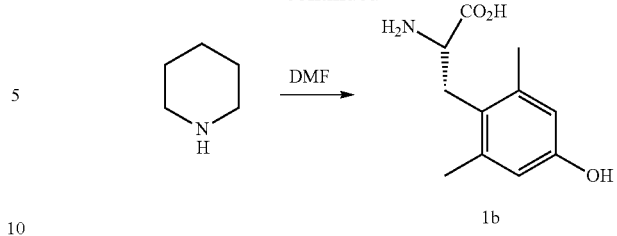

To a 250 mL rounded-bottomed flask was charged Fmoc-DMT (1a, 7 g; 0.0162 mol) followed by N,N-dimethylformamide (DMF) (91 mL). The mixture was stirred for 10 min. Piperidine (62 mL; 53.4 g; 0.628 mol; 38.8 eq.) was added to the solution at ambient temp. Precipitation was observed after 20 min. The mixture was stirred for 2 h. The bulk of the DMF was removed under reduced pressure at 65-70° C. Tert-butyl methyl ether (MTBE) (200 mL) was added to the suspension and the mixture was stirred for 16 h. The solid was collected by filtration and washed with 3×50 mL MTBE. It was allowed to dry for 4 h in vacuo at ambient temperature to afford 4.3 g white solid. The material was used "as is" for the next step.

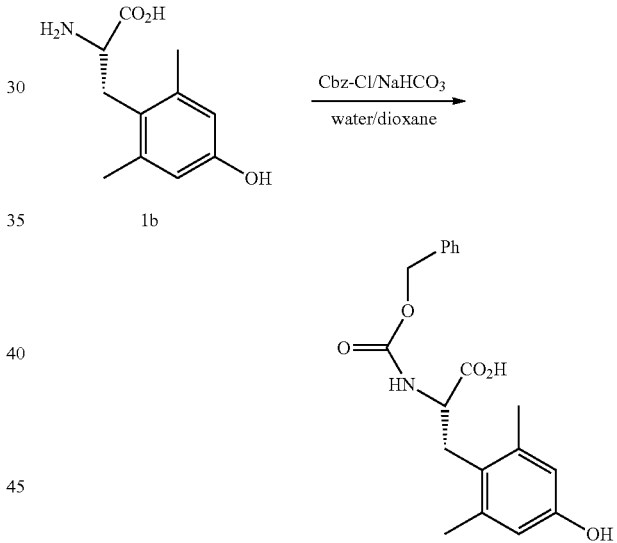

To a 1 L 1 neck rounded-bottomed flask was charged DMT (1b, 6.4 g; 30.6 mmol) (available, e.g., from Sigma-Aldrich) followed by water (320 mL) and 1,4-dioxane (85 mL). The mixture was stirred for 15 min. Sodium bicarbonate (9 g; 107.1 mmol; 3.5 eq.) was added to the solution. After 10 min benzyl chloroformate (6.6 mL; 7.9 g; 46.3 mmol; 1.5 eq.) was charged to the solution at ambient temperature. The solution was stirred for 2 h. The water/1,4-dioxane solution was then washed twice with 2×200 mL ethyl acetate. The basic water/1,4-dioxane layer was then slowly acidified with 1 M HCl (85 mL) until the observed cloudiness persisted. The product was extracted into ethyl acetate (200 mL). The ethyl acetate solution was washed with aqueous brine (100 mL). It was then allowed to stir with sodium sulfate. The drying agent was removed by filtration. The filtrate was concentrated under reduced pressure to afford 6.0 g of the title compound 1 as heavy oil. The structure was confirmed as MS indicated a molecular ion peak of 344 (m/z+H). $^1$H NMR (300 MHz, DMSO-$d_6$) δ 2.16 (s, 6H); 2.80-3.01 (m, 2H); 4.10-4.13 (m, 1H); 5.01 (s, 2H); 6.40 (s, 2H); 7.25-7.38 (m, 4H); 7.66 (d, 1H); 8.97 (s, 1H); 12.6 (br, 1H)

Example 3. Preparation of DMT-OBn HCl 10

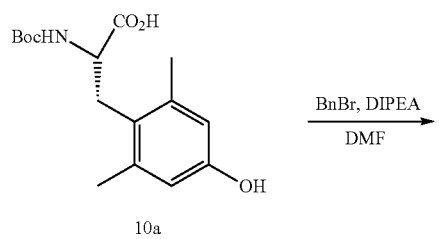

To a 500 mL rounded bottomed flask was charged Boc-DMT (10a) (10.0 g; 32.4 mmol; 1.0 equivalent). Anhydrous N,N-dimethylformamide (DMF) (100 mL; 10 vol) was charged to the flask. Diisopropylethylamine (DIPEA) (10 mL; 7.42 g; 57.5 mmol; 1.77 eq.) was charged to the solution at ambient temperature. Benzyl bromide (8.5 mL; 12.3 g; 72.0 mmol; 2.22 eq.) was charged to the homogeneous solution which was stirred for 3 days. The solution was poured into chilled water (500 mL; 5 vol). The product was extracted into ethyl acetate (300 mL). The ethyl acetate solution was washed with 2×0.1 L water. It was allowed to dry over $Na_2SO_4$ for 16 h. The filtering agent was removed by filtration and the filtrate concentrated in vacuo to afford crude oil. Heptanes (100 mL) was added to the oil and allowed to stir 10 min. It was removed by decantation to afford 15.4 g of 10b, which was used "as is" for the next step.

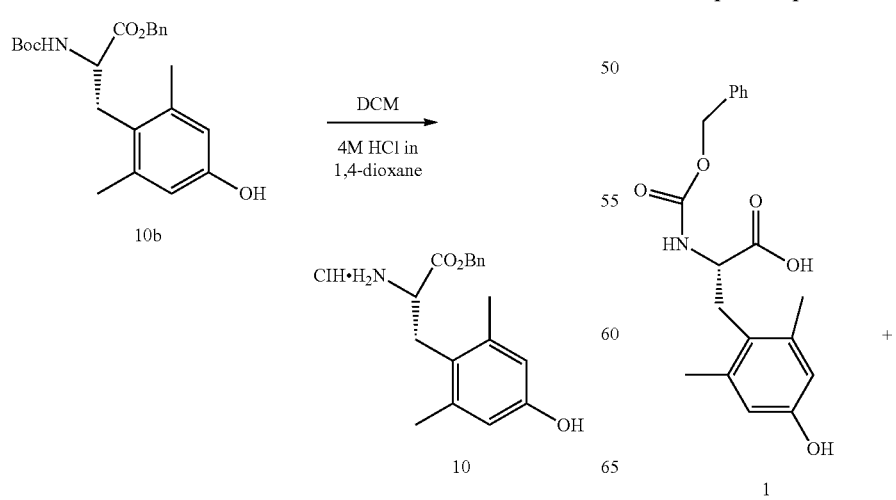

Dichloromethane (DCM) was charged to Boc-DMT-OBn (10b) (15.4 g; 38.5 mmol; 1 eq.) in a 500 mL rounded-bottomed flask. The homogeneous solution was cooled to 5° C. using an ice-water bath. At 5° C. a 4M HCl in 1,4-dioxane (48 mL; 192 mmol; 5.0 eq.) was added to the solution. The solution was stirred for 1.5 h at 0-5° C. The ice-water bath was removed and the suspension stirred at ambient temperature for 3 h. The precipitated solid was collected by filtration and washed with additional DCM (3×40 mL). It was dried in vacuo at ambient temperature to afford 9.70 g (90.0% 2-step yield) of the title compound 10. The structure was confirmed as MS indicated a molecular ion peak of 300(m/z+H). $^1$H NMR (300 MHz, DMSO-$d_6$) δ 2.13 (s, 6H); 3.06-3.09 (m, 2H); 4.00 (m, 1H); 5.04-5.09 (dd, 2H); 6.43 (s, 2H); 7.03-7.09 (m, 2H); 7.28-7.31 (m, 3H); 8.61 (m, 3H); 9.12 (s, 1H)

Example 4. Preparation of Boc-D-Arg-DMT-Lys(Boc)-Phe-NH$_2$ Via [1+2+1]

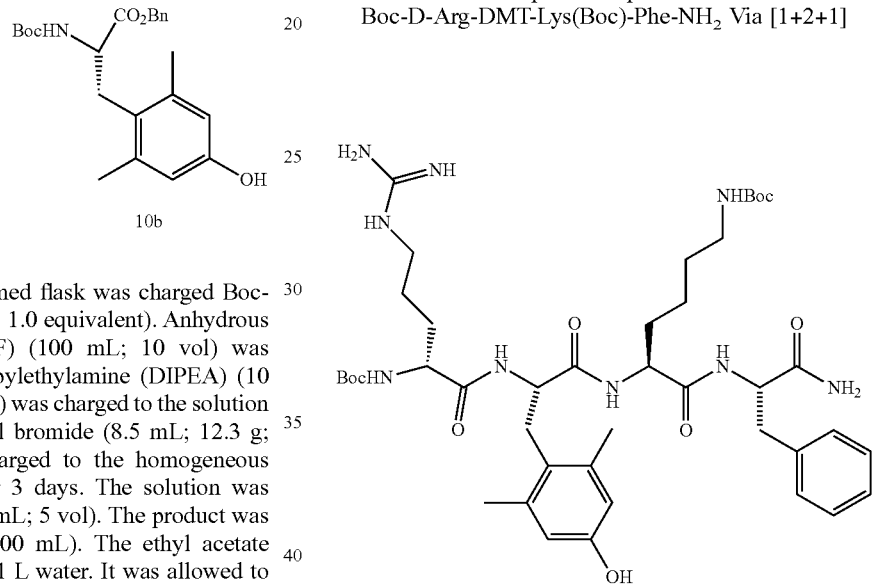

Step 1: Preparation of Cbz-DMT-Lys(Boc)-OMe

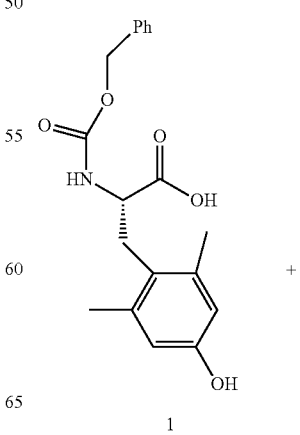

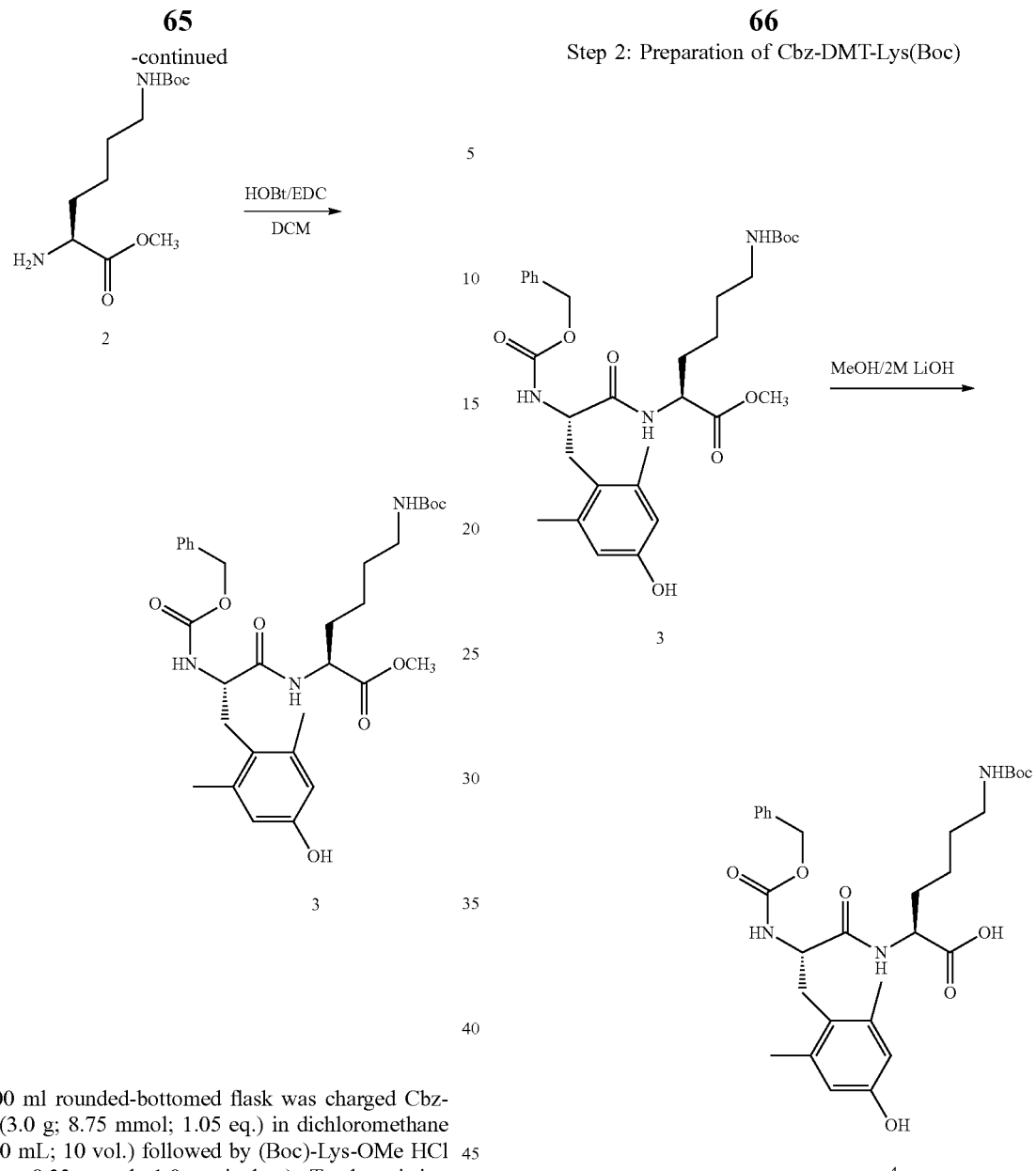

Step 2: Preparation of Cbz-DMT-Lys(Boc)

To a 500 ml rounded-bottomed flask was charged Cbz-DMT (1) (3.0 g; 8.75 mmol; 1.05 eq.) in dichloromethane (DCM) (30 mL; 10 vol.) followed by (Boc)-Lys-OMe HCl (2) (2.47 g; 8.32 mmol; 1.0 equivalent). To the stirring heterogeneous mixture was added hydroxybenzotriazole (HOBt) (1.24 g; 9.17 mmol; 1.10 eq.) followed by 1-ethyl-3-(3-dimethylaminopropyl)carbodiimide (EDCI) (1.69 g; 8.75 mmol; 1.05 eq.) and disopropylethylamine (DIPEA) (1.45 mL; 1.08 g; 8.34 mmol; 1.00 equivalent). After 16 h the DCM was removed under reduced pressure to obtain a foamy solid, which was dissolved in ethyl acetate (300 mL). The ethyl acetate solution was consecutively washed with 75 mL saturated aqueous $NaHCO_3$, 75 mL 20% brine solution, 75 mL 20% 0.1 M HCl and finally 75 mL brine solution. The ethyl acetate solution was dried with $Na_2SO_4$ (35 g). The drying agent was removed by filtration and the filtrate was concentrated under reduced pressure to afford the title compound 3 (4.0 g; 82.1%) as an off-white solid. The structure was confirmed as MS indicated a molecular ion peak of 608(m/z+Na). $^1$H NMR (300 MHz, DMSO-$d_6$) δ 1.21-1.60 (m, 6H), 1.35 (s, 9H), 2.18 (s, 6H), 2.62- (m, 1H), 2.82-(m, 3H), 3.58 (s, 3H), 4.18-4.24 (m, 2H), 4.92-5.00 (m, 2H), 6.38 (s, 2H), 6.75 (t, 1H), 7.22-7.41 (m, 5H), 8.10 (d, 1H), 8.90 (s, 1H).

Methanol (8 mL) was charged to the Cbz-DMT-Lys(Boc)-OMe (3) in a 1000 mL rounded-bottomed flask (4.0 g; 6.83 mmol). To the homogeneous solution 2M aqueous LiOH (8 mL; 16 mmol; 2.3 eq.) was added at ambient temperature. The solution was stirred for 16 h. A portion of the methanol was removed under reduced pressure. The solution was then acidified with 0.1 M HCl (140 mL; 14 mmol) until the observed precipitate persisted (pH between 2 and 3). The white solid was collected by filtration and washed with water (15 mL). It was dried in vacuo at ambient temperature to afford the title compound 4 (3.40 g; 87.2%). The structure was confirmed as MS indicated a molecular ion peak of 572 (m/z+H). $^1$H NMR (300 MHz, $CDCl_3$) δ 1.25-1.67 (m, 6H), 1.43 (s, 9H), 2.27 (s, 6H), 3.02 (br, 5H), 4.27 (br, 2H), 4.78 (br, 1H), 5.12 (s, 2H), 5.83 (br, 2H), 6.53 (s, 2H), 7.34 (m, 5H).

Step 3: Preparation of Cbz-DMT-Lys(Boc)-Phe-NH₂

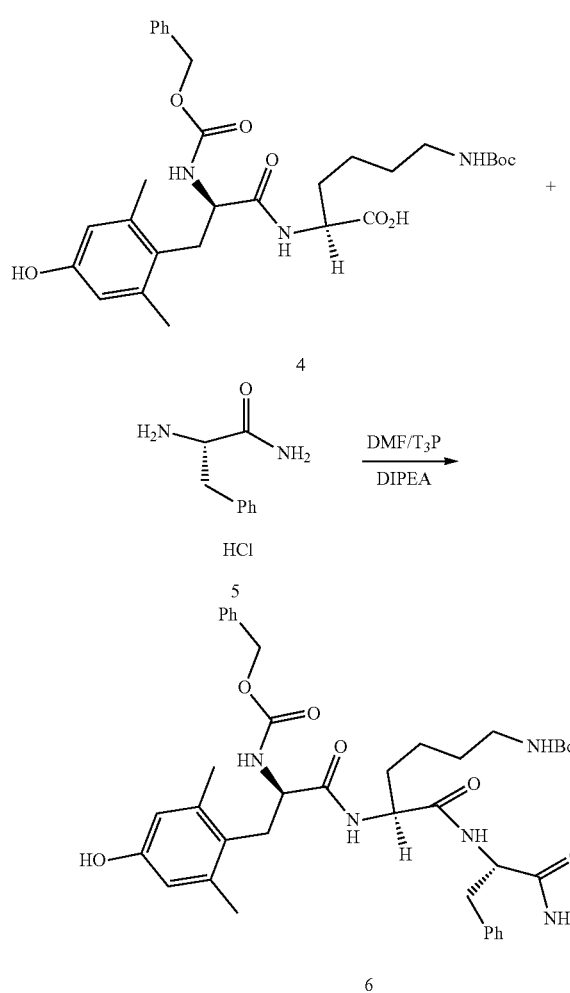

To a 100 mL rounded-bottomed flask was charged Cbz-DMT-Lys(Boc) (4) (2.0 g; 3.5 mmol; 1.0 equivalent) followed by (L)-phenylalanine amide HCl (5) (0.700 g; 3.5 mmol; 1.0 equivalent). Anhydrous N,N-dimethylformamide (DMF) (20 mL) was charged to the mixture. After complete dissolution, diisopropylethylamine (2.25 g; 3.0 mL; 17.5 mmol; 5 eq.) was charged to the homogeneous solution. After 5 min propylphosphonic anhydride (T₃P) (50% in DMF; 2.0 mL; 1.0 equivalent) was charged to the solution at ambient temperature and stirred for 3 h. Water (100 mL; 5 vol) was then charged to the solution. The resulting precipitate was filtered, washed with water (20 mL) and allowed to dry in vacuo for 16h at ambient temperature. The solid was then charged to a 100 mL rounded-bottomed flask and suspended in dichloromethane for 1 h. It was collected by filtration and was allowed to dry in vacuo at ambient temperature to afford the title compound 6 (1.80 g; 72%). The structure was confirmed as MS indicated a molecular ion peak of 718 (m/z+H) $^1$H NMR (300 MHz, DMSO-$d_6$) δ 1.13-1.54 (m, 6H); 1.33 (s, 9H); 2.14 (s, 6H); 2.65-3.01 (m, 6H); 4.10-4.18 (m, 2H); 4.34-4.41 (m, 1H); 4.77-4.99 (m, 2H); 6.33 (s, 2H); 6.70-6.74 (t, 1H); 7.05-7.48 (m, 12H); 7.79-7.92 (m, 2H), 8.93 (br, 1H)

Step 4. Preparation of DMT-Lys(Boc)-Phe-NH₂

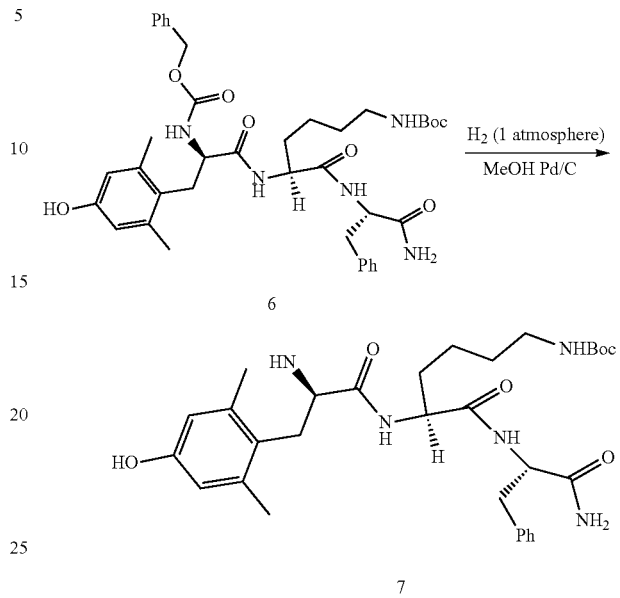

To a flask containing palladium (10 wt % on carbon powder, 50% wet with water-Degussa type, 0.044 g), was charged Cbz-DMT-Lys(Boc)-Phe-NH₂ (6) (0.2 g; 0.290 mmol) that was dissolved in methanol (4.5 mL). The flask was subjected to 3 cycles of evacuation/nitrogen gas backfill, followed by 3 cycles of evacuation/hydrogen gas backfill. The mixture was stirred under 1 atm of hydrogen for 16 h. The mixture was filtered through Celite and washed with additional methanol (20 mL). The solution was concentrated under reduced pressure to afford an oil. The oil was treated with dichloromethane (5 mL) to afford a gray solid. Dichloromethane removal by decantation, followed by drying in vacuo afforded the title compound 7 (0.140 g; 86.4%). The structure was confirmed as MS indicated a molecular ion peak of 584 (m/z+H) $^1$H NMR (300 MHz, DMSO-$d_6$) δ 1.12-1.60 (m, 6H); 1.33 (s, 9H); 2.15 (s, 6H); 2.71-3.31 (m, 6H); 4.13-4.20 (m, 1H); 4.35-4.43 (m, 1H); 4.77-4.99 (m, 2H); 6.37 (s, 2H); 6.71-6.75 (t, 1H); 7.05 (s; 1H); 7.11-7.23 (m, 5H); 7.34 (s, 1H); 7.88-7.97 (m, 2H); 8.93 (br, 1H).

Step 5: Preparation of Boc-D-Arg-DMT-Lys(Boc)-Phe-NH₂

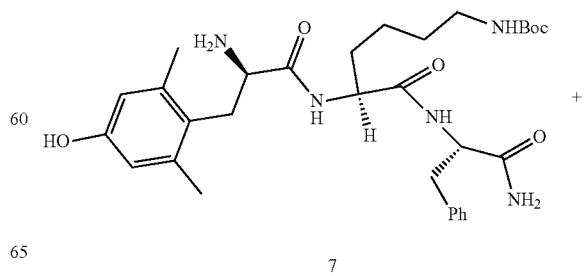

-continued

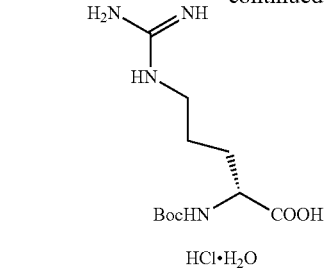
9

Example 5. Preparation of Boc-D-Arg-DMT-Lys(Boc)-Phe-NH$_2$ Via [2+2]

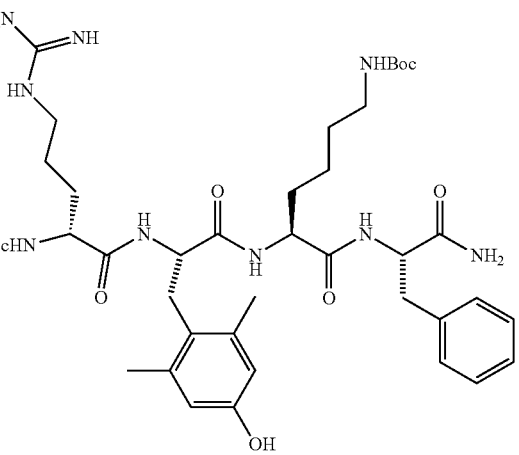

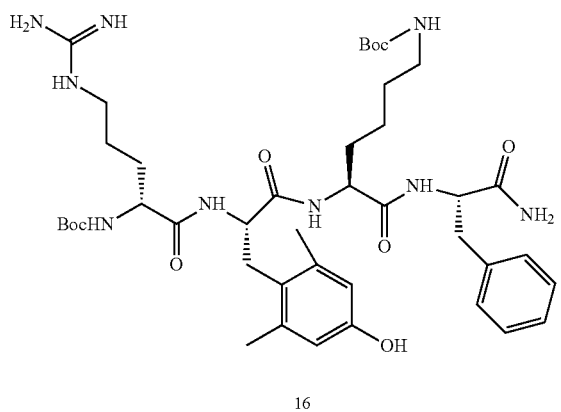
16

Step 1: Preparation of Boc-D-Arg-DMT-OBn

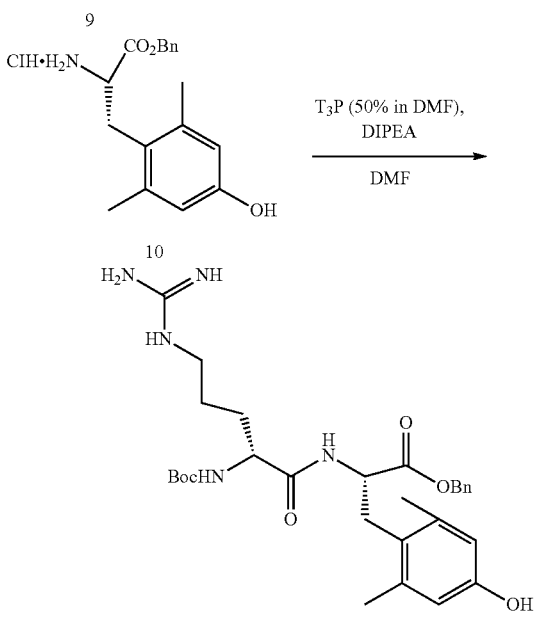

To a 50 mL rounded-bottomed flask was charged DMT-Lys(Boc)-Phe-NH$_2$ (7) (0.14 g; 0.240 mmol) followed by Boc-D-Arg HCl hydrate 9 (0.079 g; 0.240 mmol). To the solid mixture was charged N,N-dimethylformamide (DMF; 2 mL). After complete dissolution, diisopropylethylamine (DIPEA) (0.21 mL; 0.16 g; 1.21 mmol; 5.0 eq.) was added to the homogeneous solution. It was stirred for 5 min before charging propylphosphonic anhydride (T$_3$P) (50% in DMF; 1 equivalent; 0.076 g active reagent; 0.150 g active reagent with DMF; 0.14 mL active reagent with DMF) to the solution. It was stirred for 3 h before charging an additional 33% T$_3$P in DMF (0.05 mL). The solution was stirred for 1 h. Water (20 mL, 10 vol.) was charged to the solution. The solid was collected by filtration and washed with 2×2.5 mL water. The filtrate was subjected to lyophilization for 16 h to afford 0.44 g of a white solid that consisted of desired product 16 and DIPEA/T$_3$P salts. The lyophilized solid was suspended in water (6 mL) for 5 min. The solid was collected by filtration to obtain about 0.070 g solid, which was subjected to an additional water wash (2 mL) to afford the title compound 16 after filtration and drying in vacuo at ambient temperature (0.035 g; 17.5%). The structure was confirmed as MS indicated a molecular ion peak of 840(m/z+H) $^1$H NMR (300 MHz, MeOH-d$_4$) δ 1.21-1.42 (m, 23H); 1.65-1.67 (m, 5H); 2.30 (s, 6H); 2.86-3.97 (m, 8H); 3.90 (m, 1H); 4.14 (m, 1H); 4.54-4.71 (m, 2H); 6.40 (s, 2H); 7.21-7.25 (m, 5H).

To a 250 mL rounded-bottomed flask was charged DMT-OBn.HCl 10 (3.00 g, 8.93 mmol, 1.00 equivalent) followed by Boc-D-Arg HCl hydrate 9 (2.95 g, 8.97 mmol, 1.00 equivalent). Anhydrous N,N-dimethylformamide (DMF) (30 mL, 10 vol.) was added to the mixture. The resulting solution was treated with diisopropylethylamine (DIPEA), (8.00 mL, 5.94 g, 45.9 mmol, 5.12 eq.). The resulting solution was allowed to stir 5 min and then was treated drop-wise over 15 min with 50% $T_3P$ solution in DMF (5.20 mL, 5.67 g, 8.91 mmol, 1.00 equivalent). The reaction mixture was stirred for 2h at ambient temperature. The solution was then charged to chilled water (300 mL, 5° C.) and extracted with dichloromethane (DCM, 300 mL). The dichloromethane layer was washed with 0.1 M HCl (2×100 mL) and saturated brine solution (200 mL). The DCM solution was allowed to dry over anhydrous sodium sulfate (~50 g) with stirring for 16 h. The drying agent were removed by vacuum filtration and the filter cake was rinsed with DCM (4×25 mL). The organic layer was concentrated in vacuo to afford the title compound 11 (4.48 g; 90%). The structure was confirmed as MS indicated a molecular ion peak of 556 (m/z+H) $^1$H NMR (300 MHz, DMSO-$d_6$) δ 1.30-1.50 (m; 4H); 1.36 (s, 9H); 2.14 (s, 6H); 2.79-2.86 (m, 1H); 2.96-3.03 (m, 3H); 3.97-3.99 (m, 1H); 4.44-4.49 (m, 1H); 5.02 (s, 2H); 6.38 (s, 2H); 6.82 (d, 1H); 6.81-6.84 (m, 1H); 7.15-7.18 (m, 2H); 7.25-7.29 (m, 4H); 7.52-7.58 (m, 2H); 8.35 (d, 1H); 9.05 (d, 1H).

Step 3: Preparation of Boc-D-Arg-DMT

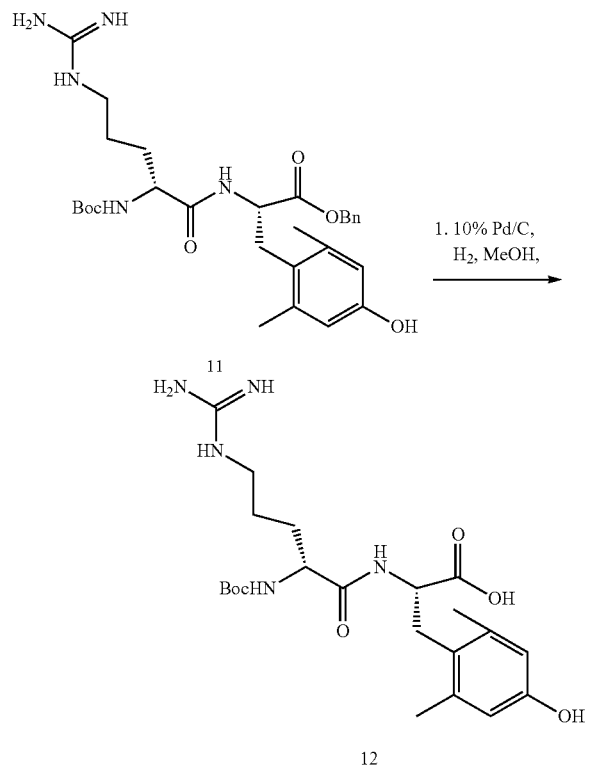

To a 100 mL rounded-bottomed flask containing palladium (10 wt % on carbon powder, 50% wet with water-Degussa type; 0.044 g), was charged Boc-D-Arg-DMT-OBn 11 (1.06 g; 1.90 mmol) that was dissolved in methanol (20 mL). The flask was subjected to 3 cycles of evacuation/nitrogen gas backfill, followed by 3 cycles of evacuation/hydrogen gas backfill. The mixture was stirred under 1 atm $H_2$ for 16 h. The mixture was filtered through Celite and washed with additional methanol (4×25 mL). The solution was concentrated under reduced pressure to afford an oily compound. The oil was treated with ethyl acetate (25 mL) and allowed to stir for 2 h. The solid was collected by filtration to afford the title compound 12 (0.74 g; 85%). The structure was confirmed as MS indicated a molecular ion peak of 466 (m/z+H) $^1$H NMR (300 MHz, DMSO-$d_6$) δ 1.20-1.50 (m; 4H); 1.36 (s, 9H); 2.20 (s, 6H); 2.74-2.83 (m, 1H); 2.97-3.08 (m, 3H); 3.97-4.06 (m, 1H); 4.39-4.41 (m, 1H); 6.39 (s, 2H); 6.82 (d, 1H); 6.86 (m, 1H); 8.13 (m, 1H).

Step 4: Preparation of CBz-Lys(Boc)-Phe-NH$_2$

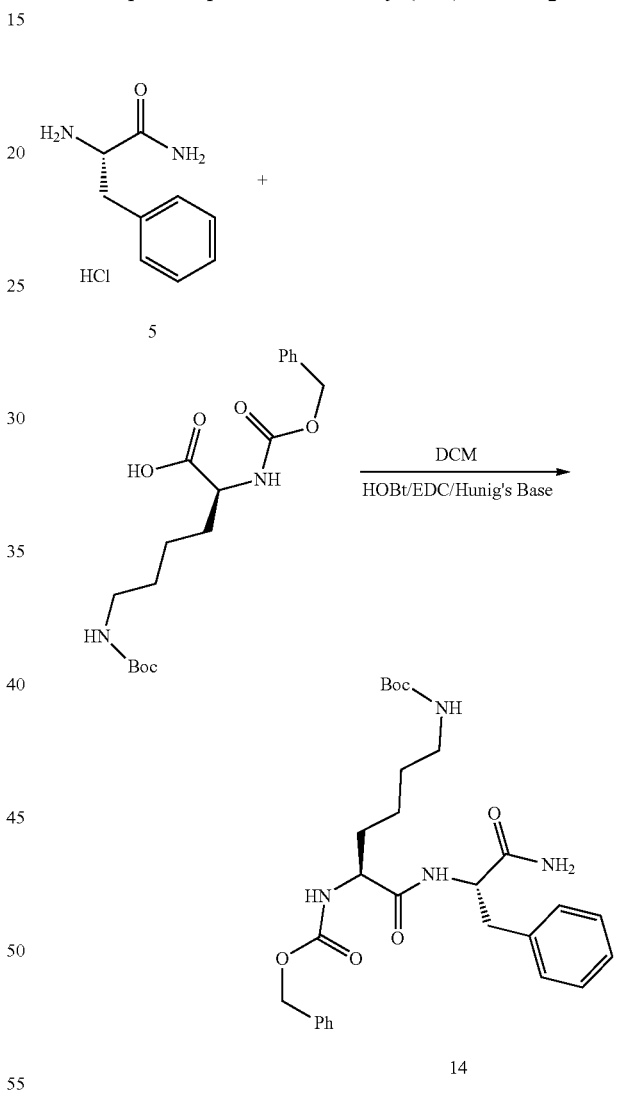

To a 50 mL 1 neck rounded-bottomed flask were charged (L)-phenylalanine amide HCl salt 5 (1 g; 4.97 mmol; 1.0 equivalent) and Cbz-Lys(Boc) 13 (1.98 g; 5.22 mmol; 1.05 eq.) followed by dichloromethane (10 mL). Hydroxybenzotriazole (HOBt) (0.74 g; 0.00548 mol; 1.10 eq.) was added followed by 1-ethyl-3-(3-dimethylaminopropyl)carbodiimide (EDCI) (1.00 g; 5.22 mmol; 1.05 eq.). Diisopropylethylamine (DIPEA) was added to the heterogeneous mixture (0.64 g; 0.86 mL; 4.97 mmol; 1.0 eq.). The suspension was transferred to a 250 mL rounded-bottomed flask and diluted with additional dichloromethane (90 mL). The heterogeneous mixture was allowed to stir 16 h. The solid was collected by filtration, and then washed with additional dichloromethane (2×25 mL) to afford white solid. It was allowed to dry in vacuo at ambient temperature to afford the title compound 14 (1.90 g; 72.5%). The structure was confirmed as MS indicated a molecular ion peak of 549(m/z+Na)$^1$H NMR (300 MHz, DMSO-d$_6$) δ 1.13-1.42 (m, 6H); 1.35 (s, 9H); 2.76-2.82 (m, 3H); 2.95-3.00 (m, 1H); 3.85-3.89 (m, 1H); 4.41-4.43 (m, 1H); 4.99 (s, 2H); 6.73 (t, 1H); 7.09-7.26 (m, 6H); 7.33-7.39 (m, 7H); 7.82 (d, 1H)

Step 5: Preparation of
NH$_2$-Lys(Boc)-L-Phe-CONH$_2$

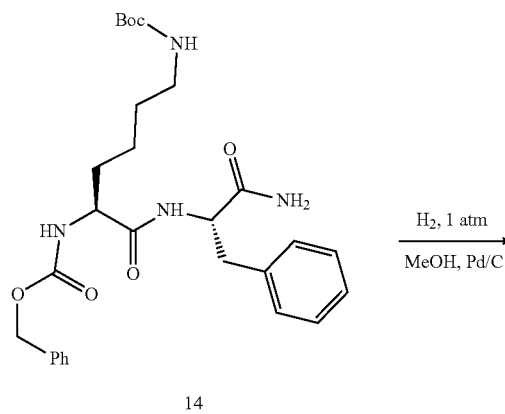

To a 100 mL rounded-bottomed flask containing palladium (10 wt % on carbon powder, 50% wet with water-Degussa type (0.140 g) was charged Cbz-Lys(Boc)-Phe-NH$_2$ 14 (0.700 g; 1.33 mmol) that was dissolved in 25 mL methanol. The flask was subjected to 3 cycles of evacuation/nitrogen gas backfill, followed by 3 cycles of evacuation/hydrogen gas backfill. The mixture was stirred under 1 atm H$_2$ for 2.5 h. The mixture was filtered through Celite (4.6 g) and washed with additional methanol (4×25 mL). The solution was concentrated under reduced pressure to afford an oil. The oil was treated with tert-butyl methyl ether (50 mL) and allowed to stir for 1 h. The resulting white solid was collected by filtration and was allowed to dry in vacuo at ambient temperature to afford the title compound 15 (0.445 g; 87.2%). The structure was confirmed as MS indicated a molecular ion peak of 393(m/z+H) $^1$H NMR (300 MHz, DMSO-d$_6$) δ 1.07-1.41 (m, 6H); 1.35 (s, 9H); 2.76-2.84 (m, 3H); 2.96-3.01 (m, 1H); 4.03-4.10 (m, 1H); 4.43-4.45 (m, 1H); 6.73 (t, 1H); 7.09-7.23 (m, 6H); 7.45 (s, 1H); 8.01-8.03 (m, 1H).

Step 6: Preparation of
Boc-D-Arg-DMT-Lys(Boc)-Phe-NH$_2$

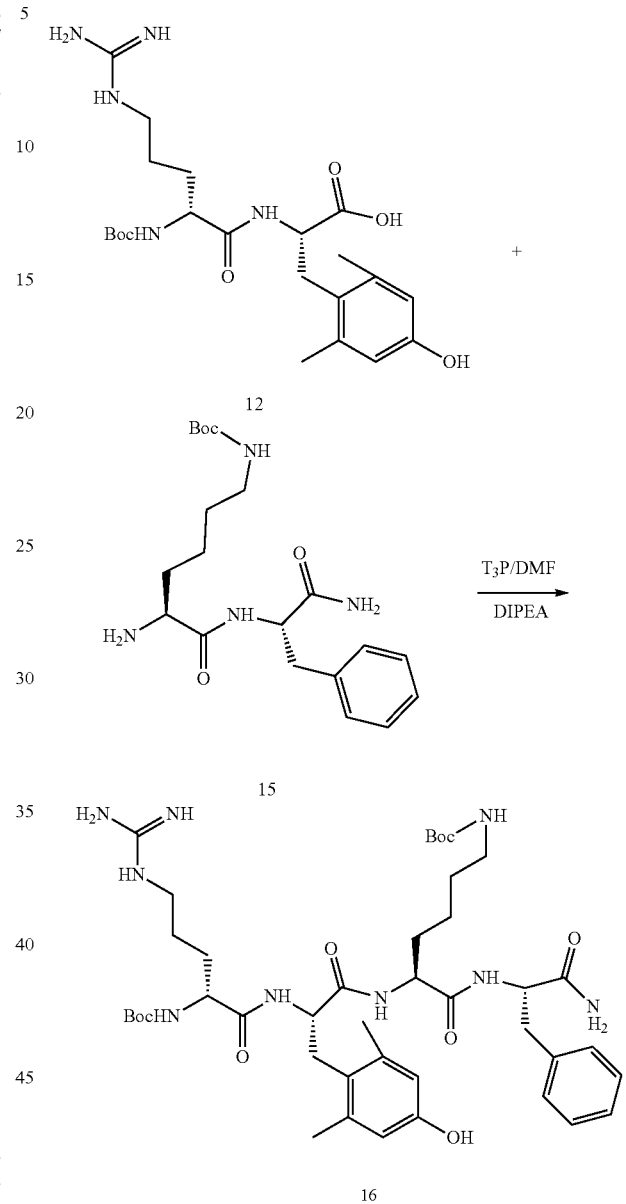

To a 50 mL 1 neck rounded-bottomed flask was charged was charged Boc-D-Arg-DMT (12) (0.1 g; 0.215 mmol; 1 equivalent) followed by Lys(Boc)-Phe-NH$_2$ (15) (0.084 g; 0.214 mmol; 1.0 eq.). Anhydrous N,N-dimethylformamide (DMF) (0.5 mL; 5 vol.) was added to the mixture. To the solution was added diisopropylethylamine (DIPEA) (0.138 g; 0.19 mL; 1.08 mmol; 5.0 eq.). After stirring for several min, propylphosphonic anhydride (T$_3$P) (50% in DMF); (1.0 eq.; 0.068 g active reagent; 0.14 g active reagent with DMF; 0.14 mL active reagent with DMF) was added to the solution. Water (10 mL) was charged to the solution after 2 h. The solid was collected by filtration and washed with water (5 mL) and allowed to dry in vacuo at ambient temperature for 3 h. It was then stirred in dichloromethane (5 mL) for 30 min., collected by filtration and dried in vacuo at ambient temperature 16 h to afford off-white solid (0.040 g; 22.2%). The structure was confirmed as MS indicated a molecular ion peak of 840(m/z+H) $^1$H NMR (300 MHz, MeOH-d$_4$) δ 1.21-1.42 (m, 23H); 1.65-1.67 (m, 5H); 2.30 (s, 6H); 2.86-3.97 (m, 8H); 3.90 (m 1H); 4.14 (m, 1H); 4.54-4.71 (m, 2H); 6.40 (s, 2H); 7.21-7.25 (m, 5H).

Example 6

Preparation of D-arginyl-2,6-dimethyl-L-tyrosyl-L-lysyl-L-phenylalaninamide

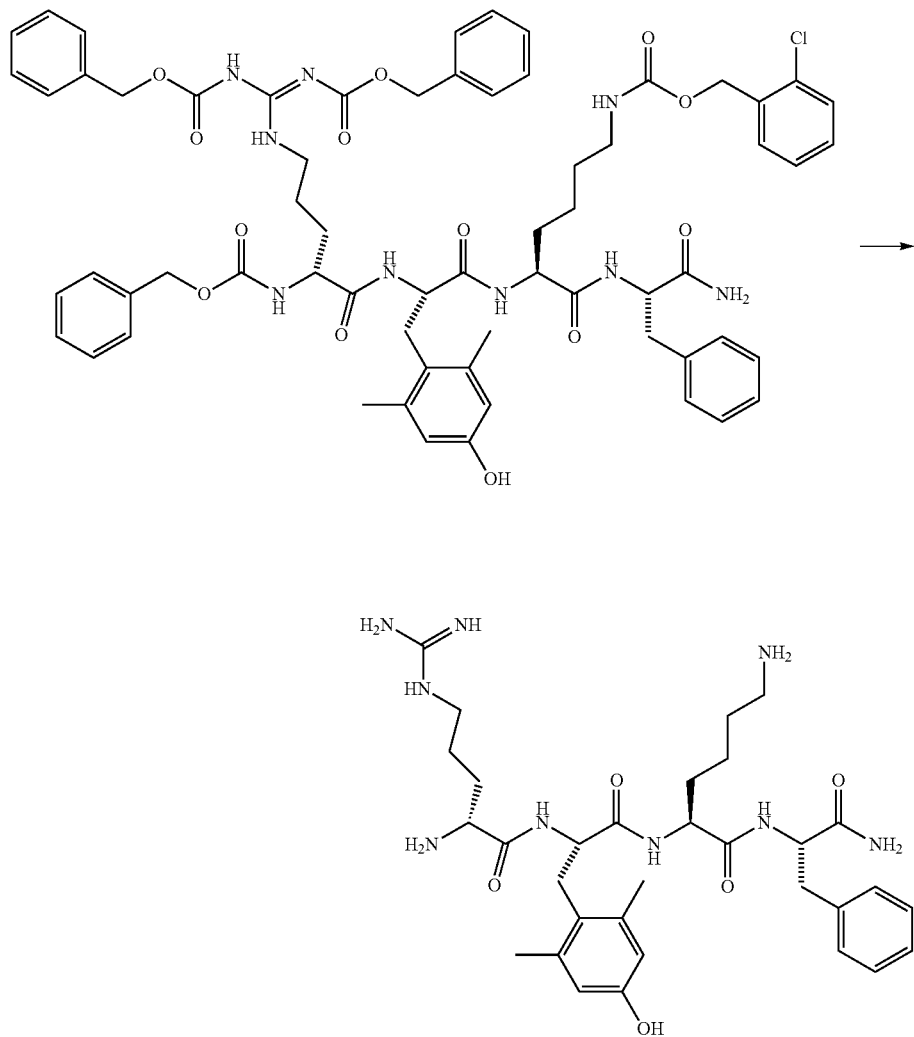

To a flask containing palladium (10 wt % on carbon powder, dry (Aldrich 520888), 0.015 g) and N$^2$-[(benzyloxy)carbonyl]-N$^5$-[{[(benzyloxy)carbonyl]amino}{[(benzyloxy)carbonyl]imino}methyl]-D-ornithyl-2,6-dimethyl-L-tyrosyl-N$^6$-{[(2-chlorobenzyl)oxy]carbonyl}-L-lysyl-L-phenylalaninamide (0.150 g, 0.124 mmol) was added methanol (5 mL) and acetic acid (0.028 ml, 0.50 mmol). The flask was subjected to 2 cycles of evacuation—hydrogen gas backfill and the mixture stirred under 1 atm of H$_2$ at 50° C. for 4 h. The mixture was cooled, filtered through Solka-Floc, and washed with additional methanol (50 mL). The combined washes were concentrated under reduced pressure and the residue lyophilized from water (20 mL) to afford the title compound (0.093 g, 99%) as a white amorphous powder. The compound was found to contain 16% w/w of acetate as determined by integration of the $^1$H NMR spectra. $^1$H NMR (400 MHz, D$_2$O) δ 1.05-1.30 (m, 4H), 1.43-1.67 (m, 6H), 1.80 (s, 6H, acetate), 2.10 (s, 6H), 2.71-3.08 (m, 8H), 3.82 (t, J=6 Hz, 1H), 4.16 (t, J=7 Hz, 1H), 4.43 (t, J=7 Hz, 1H), 4.59 (t, J=8 Hz, 1H), 6.43 (s, 2H), 7.13-7.29 (m, 5H); MS (ESI+) for C$_{32}$H$_{49}$N$_9$O$_5$ m/z 640.4 (M+H)$^+$; HPLC retention time=2.25 min.

Example 7

Preparation of D-arginyl-2,6-dimethyl-L-tyrosyl-L-lysyl-L-phenylalaninamide

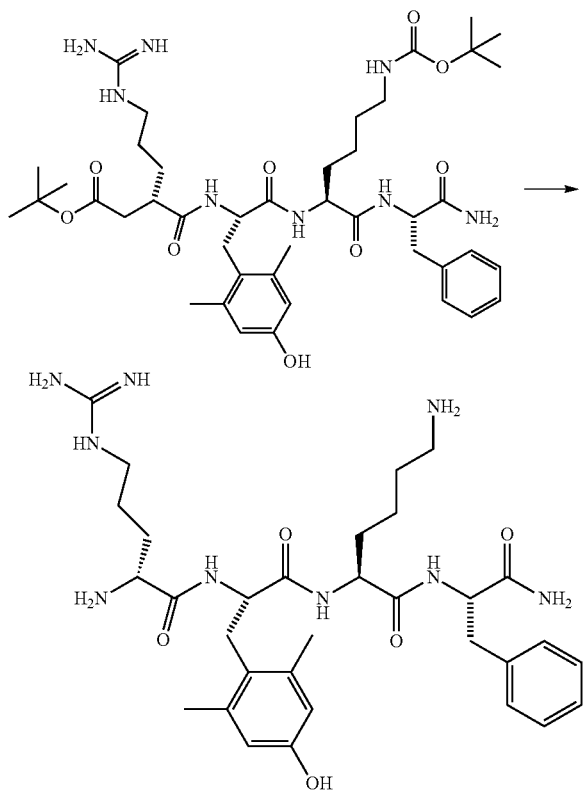

An oven-dried flask under nitrogen was charged with 7 mL isopropyl alcohol and cooled to 0-5° C. Acetyl chloride (0.85 mL, 12 mmol) was added and stirred for 15 minutes. $N^2$-[(t-butyloxy)carbonyl]-D-arginyl-2,6-dimethyl-L-tyrosyl-$N^6$-[(t-butyloxy)carbonyl]-L-lysyl-L-phenylalaninamide (1.008 g, 1.2 mmol) was added to the flask and the slurry was warmed to 40° C. and stirred for 1 h. The mixture was cooled to room temperature, filtered and washed with isopropyl acetate (3×2 mL). The collected white solid was dried in vacuo overnight. $^1$H NMR of the white solid (877.8 mg, 88% corrected yield) was consistent with the desired product and showed 1.7 wt % isopropyl alcohol and 8.1 wt % isopropyl acetate. HPLC showed a product purity of 98.0%.

All patents, patent applications, provisional applications, and publications referred to or cited herein are incorporated by reference in their entirety, including all figures and tables, to the extent they are not inconsistent with the explicit teachings of this specification.

EQUIVALENTS

Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Other embodiments are set forth within the following claims:

What is claimed is:
1. A compound that is Boc-D-Arg-DMT-OBn or a salt thereof.

* * * * *

UNITED STATES PATENT AND TRADEMARK OFFICE
CERTIFICATE OF CORRECTION

| | | |
|---|---|---|
| PATENT NO. | : 12,037,414 B2 | Page 1 of 1 |
| APPLICATION NO. | : 16/813380 | |
| DATED | : July 16, 2024 | |
| INVENTOR(S) | : Duncan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 337 days.

Signed and Sealed this
Eighth Day of July, 2025

Coke Morgan Stewart
*Acting Director of the United States Patent and Trademark Office*